United States Patent
Chen et al.

(10) Patent No.: US 11,980,763 B2
(45) Date of Patent: May 14, 2024

(54) METHOD AND SYSTEM FOR VALIDATING SAFETY OF A MEDICAL DEVICE WHEN EXPOSED TO MAGNETIC RESONANCE IMAGING FIELDS

(71) Applicant: Pacesetter, Inc., Sylmar, CA (US)

(72) Inventors: Xi Lin Chen, Valencia, CA (US); Xiyao Xin, Northridge, CA (US); Shiloh Sison, Alameda, CA (US); Shi Feng, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 211 days.

(21) Appl. No.: 17/539,235

(22) Filed: Dec. 1, 2021

(65) Prior Publication Data
US 2022/0088394 A1    Mar. 24, 2022

Related U.S. Application Data

(62) Division of application No. 16/250,895, filed on Jan. 17, 2019, now Pat. No. 11,219,770.

(51) Int. Cl.
| | |
|---|---|
| *A61N 1/37* | (2006.01) |
| *A61N 1/08* | (2006.01) |
| *A61N 1/378* | (2006.01) |
| *G01R 31/50* | (2020.01) |

(52) U.S. Cl.
CPC ........... *A61N 1/3718* (2013.01); *A61N 1/086* (2017.08); *A61N 1/3706* (2013.01); *A61N 1/378* (2013.01); *G01R 31/50* (2020.01)

(58) Field of Classification Search
CPC .............. A61M 60/148; A61M 60/139; A61M 60/174; A61M 60/237; A61M 60/414; A61M 60/804; A61M 60/818; A61M 60/81; A61M 2207/10; A61M 60/808; A61M 60/857; A61M 60/865; A61M 60/13
See application file for complete search history.

(56) References Cited

U.S. PATENT DOCUMENTS

| | | |
|---|---|---|
| 5,246,000 A | 9/1993 | Ellis et al. |
| 5,938,598 A | 8/1999 | Takeda et al. |
| 8,391,980 B2 | 3/2013 | Bornzin et al. |

(Continued)

*Primary Examiner* — Mark W. Bockelman
(74) *Attorney, Agent, or Firm* — Dean D. Small; The Small Patent Law Group, LLC

(57) ABSTRACT

A system for validating safety of a medical device in a presence of a magnetic resonance imaging (MRI) field is provided. The system includes a first electric field generating device configured to form first electric field and configured to receive a medical device at least partially within the first electric field, and a second electric field generating device configured to form a second electric field in proximity to the first electric field and configured to receive the medical device at least partially within the second electric field. One or more processors are configured to execute program instructions to calculate predicted parameter values of the medical device based on a transfer function, the transfer function defined to predict a safety characteristic of the medical device when in the presence of an MRI field, obtain measured parameter values from the medical device, the measured parameter values indicative of the safety characteristic of the medical device when exposed to the first and second electric fields, and compare the measured parameter values to the predicted parameter values in connection with validating the transfer function.

17 Claims, 14 Drawing Sheets

(56) References Cited

U.S. PATENT DOCUMENTS

| | | |
|---|---|---|
| 8,831,747 B1 | 9/2014 | Min et al. |
| 9,044,610 B2 | 6/2015 | Rosenberg et al. |
| 9,052,346 B2 | 6/2015 | Gupta et al. |
| 9,216,285 B1 | 12/2015 | Boling et al. |
| 9,232,485 B2 | 1/2016 | Wu et al. |
| 9,333,351 B2 | 5/2016 | Arnold et al. |
| 9,949,660 B2 | 4/2018 | Weinberg et al. |
| 2008/0243218 A1 | 10/2008 | Bottomley et al. |

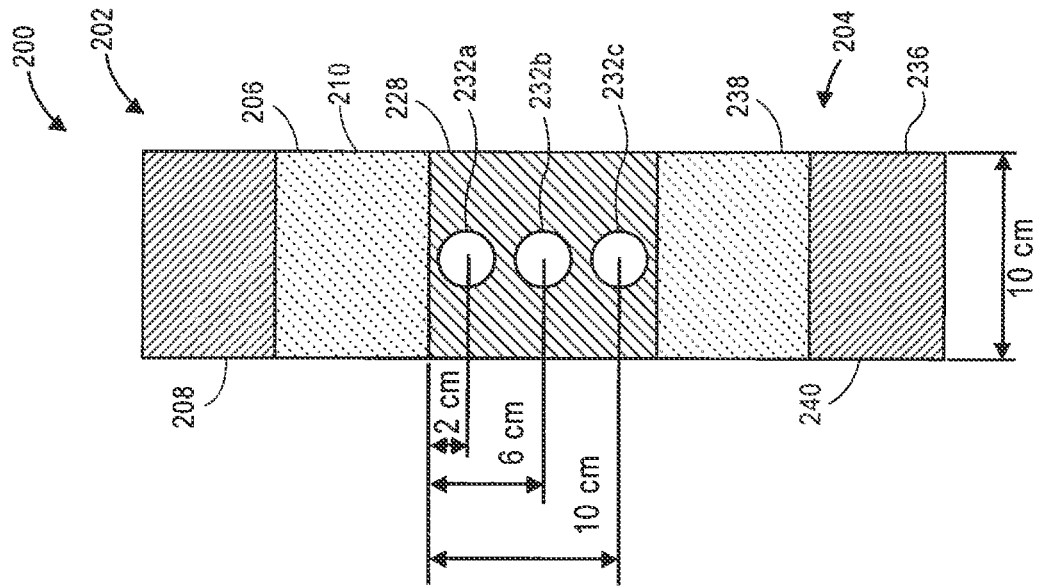
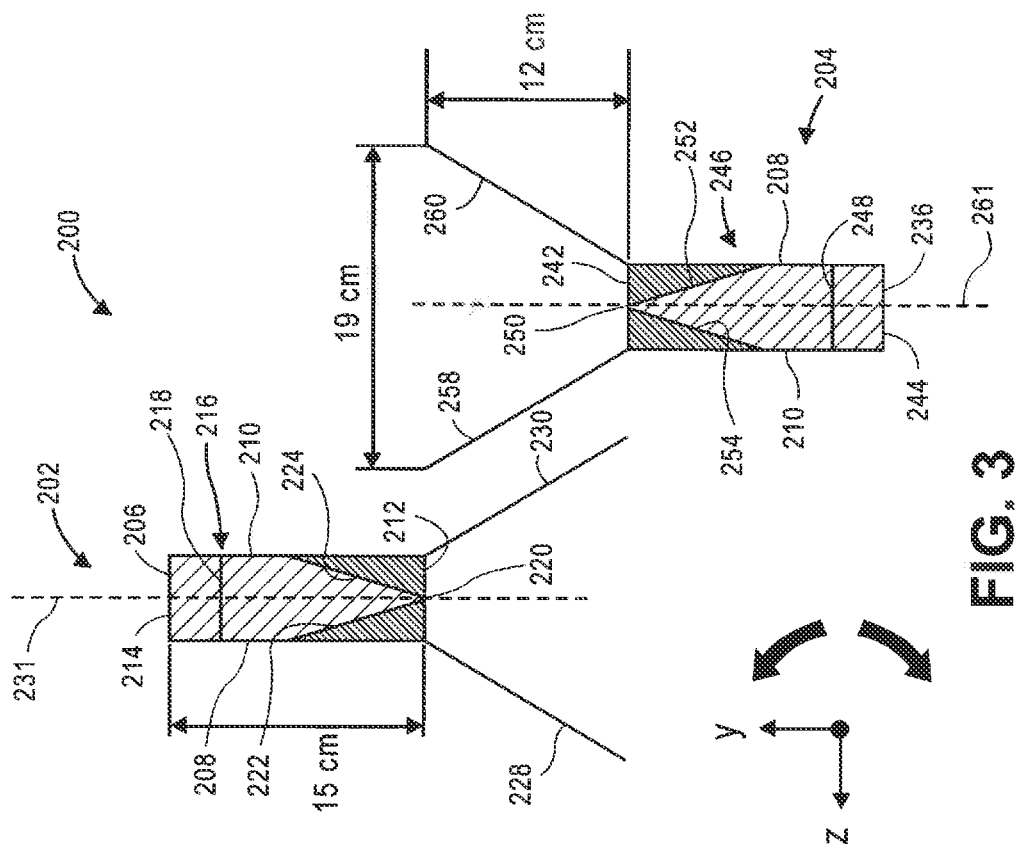

METHOD AND SYSTEM FOR VALIDATING SAFETY OF A MEDICAL DEVICE WHEN EXPOSED TO MAGNETIC RESONANCE IMAGING FIELDS

REFERENCE TO RELATED APPLICATIONS

The present application is a divisional application of, and claims priority to, U.S. application Ser. No. 16/250,895, Titled "METHOD AND SYSTEM FOR VALIDATING SAFETY OF A MEDICAL DEVICE WHEN EXPOSED TO MAGNETIC RESONANCE IMAGING FIELDS" which was filed on 17 Jan. 2019, the complete subject matter of which is expressly incorporated herein by reference in its entirety.

BACKGROUND

Embodiments of the present disclosure generally relate to a system and method of validating a transfer function related effects of a magnetic resonance imaging on an implantable medical device.

An implantable medical device (IMD) is a medical device that is configured to be implanted within a patient anatomy and commonly employs one or more electrodes, or leads, that either receive or deliver voltage, current or other electromagnetic pulses from or to an organ or tissue for diagnostic or therapeutic purposes. In general, IMDs include a battery, electronic circuitry, a pulse generator, a transceiver and/or a microprocessor that is configured to handle communication with an external instrument as well as control patient therapy. The components of the IMD are hermetically sealed within a metal housing. The IMD is completely enclosed within the human body.

Magnetic resonance imaging (MRI) is an imaging technique that utilizes strong magnetic fields, magnetic field gradients, and radio frequencies (RF) to create images of a person's anatomy. In particular, often a superconducting magnet operates in conjunction with a RF coil to create a magnetic field that can range between 0.2 Tesla to 7 Tesla.

Difficulties arise when a patient with an IMD undergoes an MRI scan. In particular, the magnetic field and strength of the incident electric field effects the temperature and voltage on the leads of the leads of the IMDs. Such heat and voltage can be detrimental to the leads of an IMD, including resulting in shorts. As a result, transfer functions have been developed to determine the effect an electric field of different MRIs will have on the IMD. Specifically, numerous MRI's of varying electric field strength have been developed. Table 1 below shows the magnetic field strength in Tesla and associated Lamor frequencies in Mega Hertz (MHz) of typical MRI machines.

| $B_0$ (T) | Frequency (MHz) |
|---|---|
| 0.2 | 8.5 |
| 0.3 | 12.8 |
| 0.4 | 17.0 |
| 0.7 | 29.8 |
| 1.2 | 51.1 |
| 1.5 | 63.9 |
| 3 | 127.7 |
| 7 | 298.1 |

In an MRI safety assessment related to an IMD, lead radio RF heating tests, and device RF induced voltage tests are the most complex testing among testing requirements. Consequently, for devices with leads, the transfer function that governs the interaction of the lead and the MRI exposure field is required to be validated. A commonly adopted validation procedure is to subject the device (lead and pulse generator) to RF exposure in a saline-filled ASTM phantom placed in a MRI RF coil. The lead needs to be placed along various pathways which cover a range of diversified incident electric field patterns (with varying phase and magnitude distributions). The transfer function is to be validated by comparing the predictions of electrode heating or header voltage to actual measurements in the ASTM phantom.

However, the process remains difficult, time consuming, and expensive. A need remains for improved methods and devices for validating the transfer function for IMDs associated with an MRI.

BRIEF SUMMARY

In an example embodiment, a system for validating safety of a medical device in a presence of a magnetic resonance imaging (MRI) field is provided. The system includes a first electric field generating device configured to form first electric field and configured to receive a medical device at least partially within the first electric field, and a second electric field generating device configured to form a second electric field in proximity to the first electric field and configured to receive the medical device at least partially within the second electric field. One or more processors are configured to execute program instructions to calculate predicted parameter values of the medical device based on a transfer function, the transfer function defined to predict a safety characteristic of the medical device when in the presence of an MRI field, obtain measured parameter values from the medical device, the measured parameter values indicative of the safety characteristic of the medical device when exposed to the first and second electric fields, and compare the measured parameter values to the predicted parameter values in connection with validating the transfer function.

Optionally, the first electric field generating device includes a first plate in parallel spaced relation to a second plate disposed within a housing, and the first electric field generating device further includes a first angled surface extending from the first plate to an opening in the housing and a second angled surface extending from the second plate to the opening. An electric charge is placed on the first and second plates, and the first electric field is formed exterior to the housing adjacent the opening. In another aspect, the medical device is an implantable medical device that includes a lead, and the first electric field generating device further includes a first receiving section extending from the housing at an angle to the first plate that is configured to receive the lead of the implantable medical device, and a second receiving section extending from the housing at an angle to the second plate and extending away from the first receiving section that is configured to receive the lead of the implantable medical device.

In another aspect the first receiving section has openings disposed therethrough and configured to receive the lead of the implantable medical device, and the second receiving section having openings disposed therethrough and configured to receive the lead of the implantable medical device. In another example the first electric field generating device further includes a power source module for providing an electric current to the first plate and the second plate, and configured to vary amplitude, phase, and frequency of the first electric field. Optionally, the system also includes a phantom including a substrate that receives the first receiving section and the second receiving section.

Optionally, the first electric field generating device is a first coil configured to form the first electric field, and the second electric field generating device is a second coil that is configured to form the second electric field.

In yet another aspect, the system also includes a third electric field generating device configured to form a third electric field in proximity to the first electric field and second electric field and configured to receive a lead of a medical device.

In another example embodiment, a system for validating safety of a medical device in a presence of a magnetic resonance imaging field is provided. The system includes a first electric field generating device configured to form electric field and configured to receive a medical device at least partially within the first electric field, and a second electric field generating device configured to form a second electric field in proximity to the first electric field and configured to receive the medical device at least partially within the second electric field. The system also includes an output configured to generate measured parameter values from the medical device, the measured parameter values indicative of a safety characteristic of the medical device when exposed to the first and second electric fields.

In one aspect, the first electric field generating device includes a first plate in parallel spaced relation to a second plate disposed within a housing, and the first electric field generating device further includes a first angled surface extending from the first plate to an opening in the housing and a second angled surface extending from the second plate to the opening. When an electric charge is placed on the first and second plates, the first electric field is formed exterior to the housing adjacent the opening.

Optionally, the medical device is an implantable medical device that includes a lead. In an example, the first electric field generating device further includes a first receiving section extending from the housing at an angle to the first plate that is configured to receive the lead of the implantable medical device, and a second receiving section extending from the housing at an angle to the second plate and extending away from the first receiving section that is configured to receive the lead of the implantable medical device.

In another example embodiment a method of validating safety of a medical device in a presence of a magnetic resonance imaging field is provided. the method includes forming a first electric field with a first electric field generating device, forming a second electric field with a second electric field generating device, and inserting at least a portion of the medical device into the first electric field and into the second electric field at a first position. The method also includes recording a first measured parameter value of the lead in the first electric field and second electric field in the first position, changing at least one of the medical device position in at least one of the first electric field or the second electric field, the first electric field, or the second electric field, and recording a second measured parameter value of the lead in the first electric field and second electric field after changing the at least one of the medical device position in at least one of the first electric field or the second electric field, the first electric field, or the second electric field.

In another aspect, the method also includes, comparing the recorded first measured parameter value of the medical device to a first predicted parameter value of the lead that is based on a transfer function to determine a first error, and comparing the recorded second measured parameter value of the medical device to a second predicted parameter value of the medical device that is based on the transfer function to determine a second error. Alternatively, the method also includes validating the transfer function based on a model formed utilizing the first error and the second error.

Optionally, changing at least one of the medical device position in at least one of the first electric field or the second electric field, the first electric field, or the second electric field includes varying a power source to vary an amplitude, phase, or frequency of the first electric field or second electric field.

In one aspect, the first electric field generating device is configured to provide the first electric field adjacent an elongated opening in a front panel of the first electric field generating device and the second electric field generating device is configured to provide the second electric field adjacent an elongated opening in a front panel of the second electric field generating device. In an example, the medical device has at least one lead that includes a first section and a second section, and in the first position the first section of the lead is parallel to the front panel of the first electric field generating device, and in the first position the second section of the lead is parallel to the front panel of the second electric field generating device. Alternatively, in the second position the first section of the lead is angled relative to the front panel of the first electric field generating device, and in the second position the second section of the lead is angled relative to the front panel of the second electric field generating device.

In an example, the first measured parameter value of the medical device is one of medical device temperature, power, e-field, h-field or medical device voltage, current. Optionally, changing the at least one of the medical device position in at least one of the first electric field or the second electric field, the first electric field, or the second electric field includes varying amplitude, or phase, or frequency of the first electric field and/or second electric field. Alternatively, the first electric field is configured to change from a first frequency to a second frequency; and wherein the second electric field is configured to change from a first frequency to a second frequency.

BRIEF DESCRIPTION OF THE DRAWINGS

FIG. 3 illustrates a top plan view of a validation system operated in accordance with embodiments herein.

FIG. 4 illustrates a side plan view of a validation system operated in accordance with embodiments herein.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Embodiments herein provide methods and systems of validating a plurality of transfer functions utilizing a single validation system. In particular, numerous example validation systems are illustrated, each configured to receive a medical device, such as an IMD, in numerous different positions while also providing at least two different electric fields where each electric field may include varied amplitudes, phases, and frequencies. In this manner, multiple variables of the transfer function may be measured simultaneously. Specifically, the amplitude, phase, and frequency of each electric field in addition to the position of the medical device within each electric field may be varied. In examples when the medical device includes a flexible lead, the lead may be bent such that varying sections of the lead may be positioned in different positions in each electric field, providing addition variables to be measured.

Each validation system also includes one or more processors that determine the effect each section of the lead has in each electrical field formed in relation to parameters of the lead such as at least temperature and voltage. The one or more processors then plot the value of a parameter along the medical device and compares the actual value to that the estimated by a transfer function. In one example the one or more processors overlay the actual parameter values compared to that estimated by the transfer function. The electric field may then by varied to provide additional parameters for review of the transfer function. Thus, a medical device may be validated for during a single test by merely repositioning the lead and varying electric fields. Consequently, expensive RF validating coils and testing procedures are unneeded and eliminated reducing cost and improving efficiencies.

Figure 1:
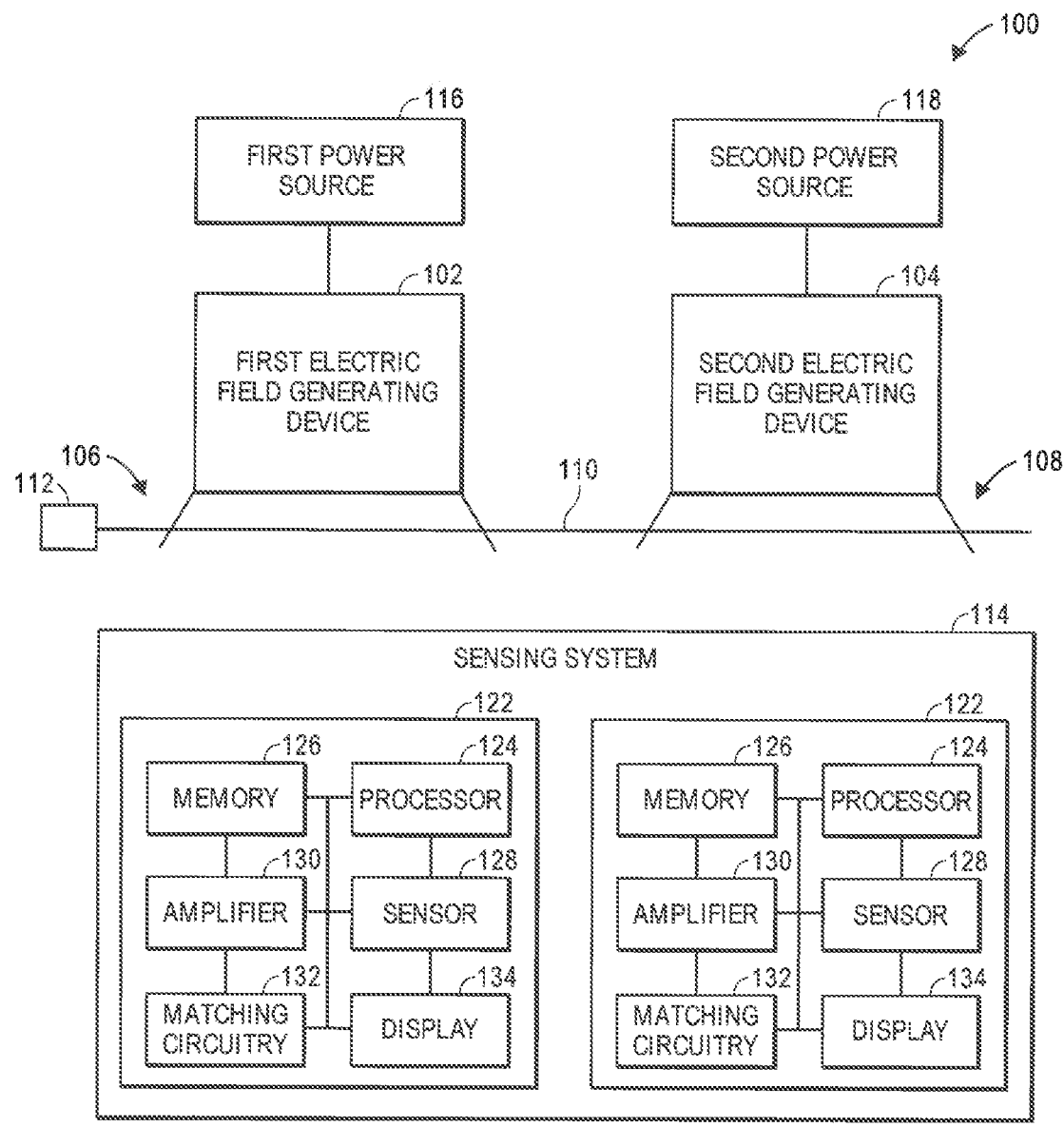
FIG. 1 illustrates a simplified block diagram of a validation system operated in accordance with embodiments herein.

FIG. 1 illustrates a simplified block diagram of a validation system 100 operated in accordance with embodiments herein to validate the safety of an implantable lead when exposed to magnetic resonance imaging fields. The system 100 includes a first electric field generating device 102 located in close proximity to a second electric field generating device 104. The system 100 also includes a first receiving region 106 and a second receiving region 108. The first receiving region 106 is configured to receive a lead 110 of an IMD 112 in a plurality of positions within a first electric field formed by the first electric field generating device 102. Similarly, the second receiving region 108 is configured to receive the lead 110 of the IMD 112 in a plurality of positions within a second electric field formed by the second electric field generating device 104. The validation system 100 additionally includes a sensing system 114 for determining parameter of the lead 110 of the IMD 112 resulting from the electric field and communicating the effects to a user or clinician.

The first electric field generating device 102 includes a first power source 116 that provides current for generating the first electric field. In one example the first power source 116 provides a variable input to vary the electric field. Alternatively, the first power source 116 is constant and a current regulating device varies current to again provide an adjustable or variable input to vary the electric field. In an example the input frequency to arrive at the first electric field range is between 5 Mega Hertz (MHz) and 300 MHz to provide the electric field. In yet another example the power source operates at 1 Watt (1 W). In this manner, a large range of electric fields may be generated the includes similar fields generated by numerous MRI devices in an inexpensive manner. Such electric devices include parallel plate devices, toroid coil devices, solenoid coil devices, and the like, several of which are provided in the examples of FIGS. 16-20.

The second electric field generating device 104 includes a second power source 118 that provides current for generating the first electric field. In one example the first power source 116 and second power source 118 are a single power source. In an alternative example to separate power sources 116 and 118 are presented. In one example the second power source 118 provides a variable input to vary the electric field. Alternatively, the second power source 118 is constant and a current regulating device varies current to again provide an adjustable or variable input to vary the electric field. In an example the input frequency to arrive at the first electric field range is between 5 Mega Hertz (MHz) and 300 MHz to provide the electric field. In this manner, a large range of electric fields may be generated the includes similar fields generated by numerous MRI devices in an inexpensive manner. Such electric devices include parallel plate devices, toroid coil devices, solenoid coil devices, and the like, several of which are provided in the examples of FIGS. 16-20. Additionally, while in this example and other examples described herein only two electric field generating devices are presented, three, four, and more electrical field generating devices may be provided, each additional electric field generating device providing additional data points or readings related to the lead 110 of the IMD 112 that may be compared against an expected reading generated by a transfer function. Thus, the transfer function is validated.

The first and second receiving sections 106 and 108 are each configured to receive the lead 110 of IMD 112 in numerous different positions within the corresponding electric field formed by a corresponding electric field generating device 102 or 104. In one example the first receiving region 106 is part of and extends from the first electric field generating device 102 while the second receiving region 108 is part of and extends from the second electric field generating device 104. Alternatively, the first receiving region 106 is coupled to the first electric field generating device 102 while the second receiving region 108 is coupled to the second electric field generating device 104. Yet alternatively, in another example the first receiving region 106 is spaced in close proximity to the first electric field generating device 102 while the second receiving region 108 is spaced in close proximity to the second electric field generating device 104. Similarly, combination of these arrangements may be provided.

The lead 110 in one example is a flexible lead. In particular, the lead 110 may be shaped to provides a plurality of sections. In one example two sections are provided. Still, because the lead 110 is flexible, in other examples more sections may be presented. Alternatively, less sections may be formed, such as when the lead 110 is unbent and straight as illustrated. In each example, each section is placed in a position in relation to each electric field generated by the field generating devices 102, 104. The lead 110 may then be bent and repositioned within each electric field as a result of the design of the corresponding receiving sections 106 and 108.

The IMD 112 in one example may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference. Additionally or alternatively, the IMD 101 may be a leadless monitor, examples of which are disclosed in U.S. Patent Application having U.S. patent application Ser. No., 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference. Non-limiting examples of IMDs include one or more of neurostimulator devices, implantable leadless monitoring and/or therapy devices, and/or alternative implantable medical devices.

The sensing system 114 includes one or more computing devices 122 that each include one or more processors 124 with a memory 126 that includes instructions that are performed by the one or more processors 124. The one or more computing devices 122 also includes at least one sensor 128 that detect the first electric field and second electric field and detect the parameters of the IMD 112 and specifically the lead 110 as a result of the first and second electric fields. In one example the sensor 128 measures the voltage on the IMD 112. In another example the sensor 128 measures the temperature of the IMD 112. In yet another example both a voltage sensor and a temperature sensor are provided.

The sensing system 114 additionally includes amplifiers 130 in communication with matching circuitry 132 for the electric field generating devices 102 and 104. The one or more processors 124 are thus also configured to communicate such parameters, to a user. In one example the one or more processors 124 display the information received by the at least one sensor 128 on a display 134 or interface of the one or more computing devices 122. In one example the sensor 128 readings are plotted on a graph. In yet another example the plotted graph is plotted over a graph of expected reading as determined by a corresponding transfer function and provided by the matching circuitry 132. In yet another example the results may be printed, communicated over emails, saved in the cloud, and the like.

Figure 2:
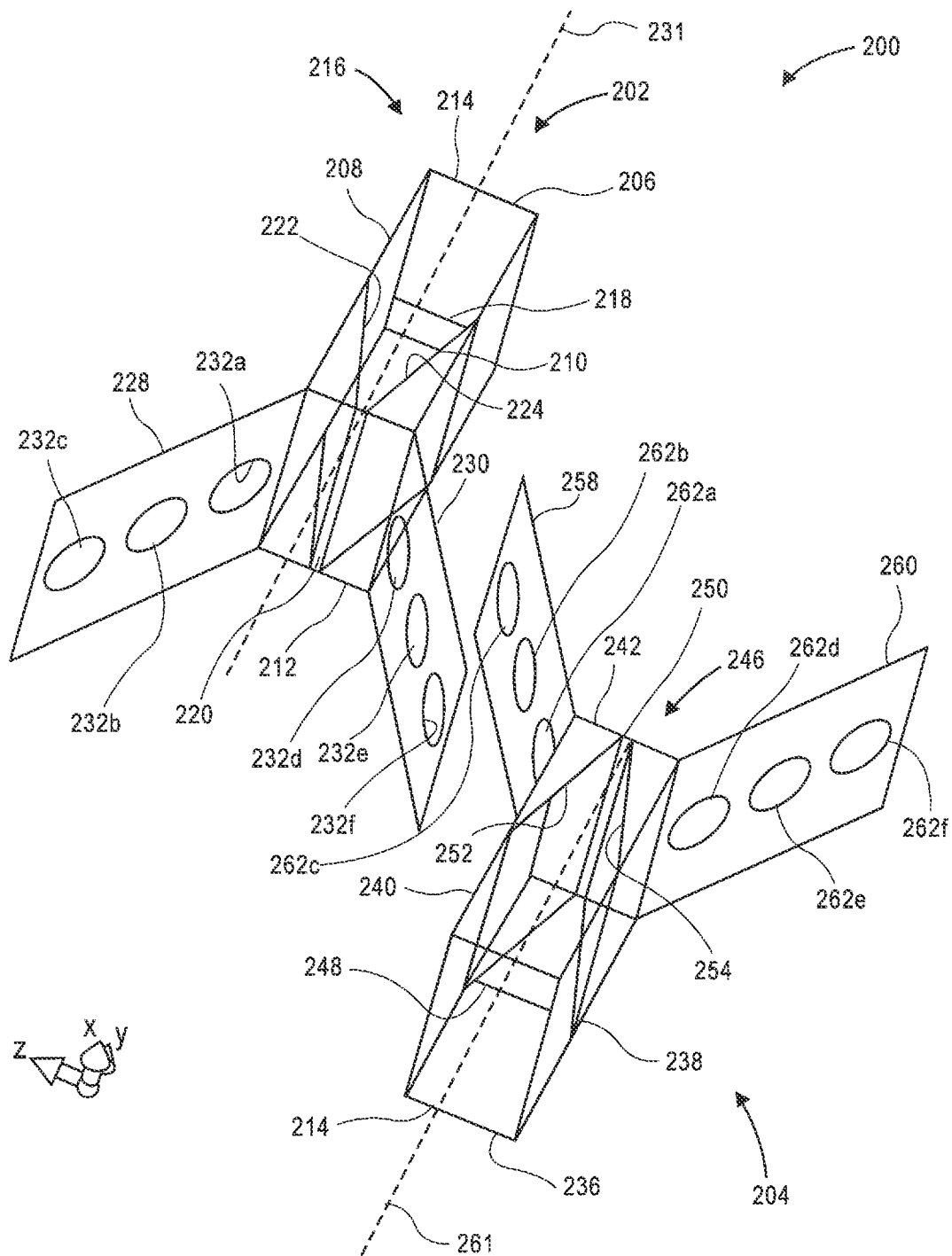
FIG. 2 illustrates a perspective view of a validation system operated in accordance with embodiments herein.

FIG. 2 illustrates a perspective view of an example validation system 200 used to validate the safety of a medical device when exposed to magnetic resonance imaging fields. FIG. 3 illustrates a top view of the example validation system 200. FIG. 4 illustrates a side view of the example validation system 200. In one example the validation system 200 is the validation system 100 of FIG. 1.

The validation system 200 includes a first electric field generating device 202 located in close proximity to a second electric field generating device 204. In this example, a sensor system is not illustrated in order to provide additional detail related to the first electric field generating device 202 and second electric field generating device 204.

The first electric field generating device 202 of FIGS. 2-4 includes a first housing 206 that includes a first plate 208 in parallel spaced relation to a second plate 210 both secured to a front panel 212 and a back panel 214 to define an interior cavity 216. In one example the first plate 208, second plate 210, front panel 212, and back panel 214 are of one piece construction. Alternatively, the first plate 208, second plate 210, front panel 212, and back panel 214 are joined or coupled together through a fastening method such as welding. The first plate 208 and second plate 210 in one example the first and second plates 208, 210 comprise a metallic material such that when current is run through the plates 208, 210, the first plate presents a first charge, such as in one example a positive charge, while the second plate presents a second charge that is an opposite charge to the charge of the first plate, and in one example a negative charge. In this manner an electric field is generated or formed within the interior cavity 216 in the housing 206 between the first and second parallel plates 208 and 210.

A feed or power source 218 is electrically coupled to the first and second plates 208 and 210. In one example the power source 218 is a variable current source wherein an increase in the current flowing through the first and second plates 208 and 210 may be controlled to vary the amplitude, phase, and frequency of the electric field between the first and second plates 208 and 210. In this manner numerous varying electric fields may be formed by the first electric field generating device 202. In another example, the power source is constant and a regulating device or controller controllably alters the current flowing to the first and second plates 208, 210, again to provide numerous electric fields formed by the first electric field generating device 202.

The front panel 212 in one example includes an elongated guiding slot 220 disposed therethrough. Specifically, disposed within the defined interior cavity 216 are a first angled surface 222 and a second angled surface 224. The first angled surface 222 tapers from the first plate 208 to the elongated guiding slot 220 while the second angled surface 224 similarly tapers from the second plate 210 to the elongated guiding slot 220. In this manner the first angled surface 222 and second angled surface 224 taper toward one another with each terminating on either side of the elongated guiding slot 220. As a result of the first angled surface 222 and second angled surface 224, the formed electric field is emitted from the interior cavity 216 defined in the housing 206 through the elongated guiding slot 220 to provide a corresponding first electric field 226 (FIG. 6) proximate to the elongated guiding slot 220.

A first receiving section 228 and a second receiving section 230 extend from the housing 206. In an example the first receiving section 228 and second receiving section 230 are fan out plates with the first electric field 226 (FIG. 6) formed between the first receiving section 228 and second receiving section 230. In one example the first receiving section 228 and second receiving section 230 both extend at an angle from the housing away from the housing 206 and away from a center axis 231 formed through the elongated guiding slot 220. In this manner the first receiving section 228 and second receiving section 230 extend along diverging pathways away from the housing 206. In one example the first receiving section 228 and second receiving section 230 are each of one piece construction with the housing 206. Alternatively, the first receiving section 228 and second receiving section 230 are each mechanically coupled to the housing 206.

The receiving sections 228 and 230 have a plurality of openings 232a-232f where the openings 232a-232f are configured to receive a lead of an IMD. In one example the centers of the first openings 232a and 232d of the receiving sections 228 and 230 are two centimeters from the front panel 212 while the centers of the second openings 232b and 232e are 6 cm from the front panel 212, and the centers of the final or third openings 232c and 232f of each receiving section 228 and 230 are 10 cm from the front panel 212. In this manner, the centers of the openings are approximately 4 cm from a next corresponding center of an opening.

Figure 6:
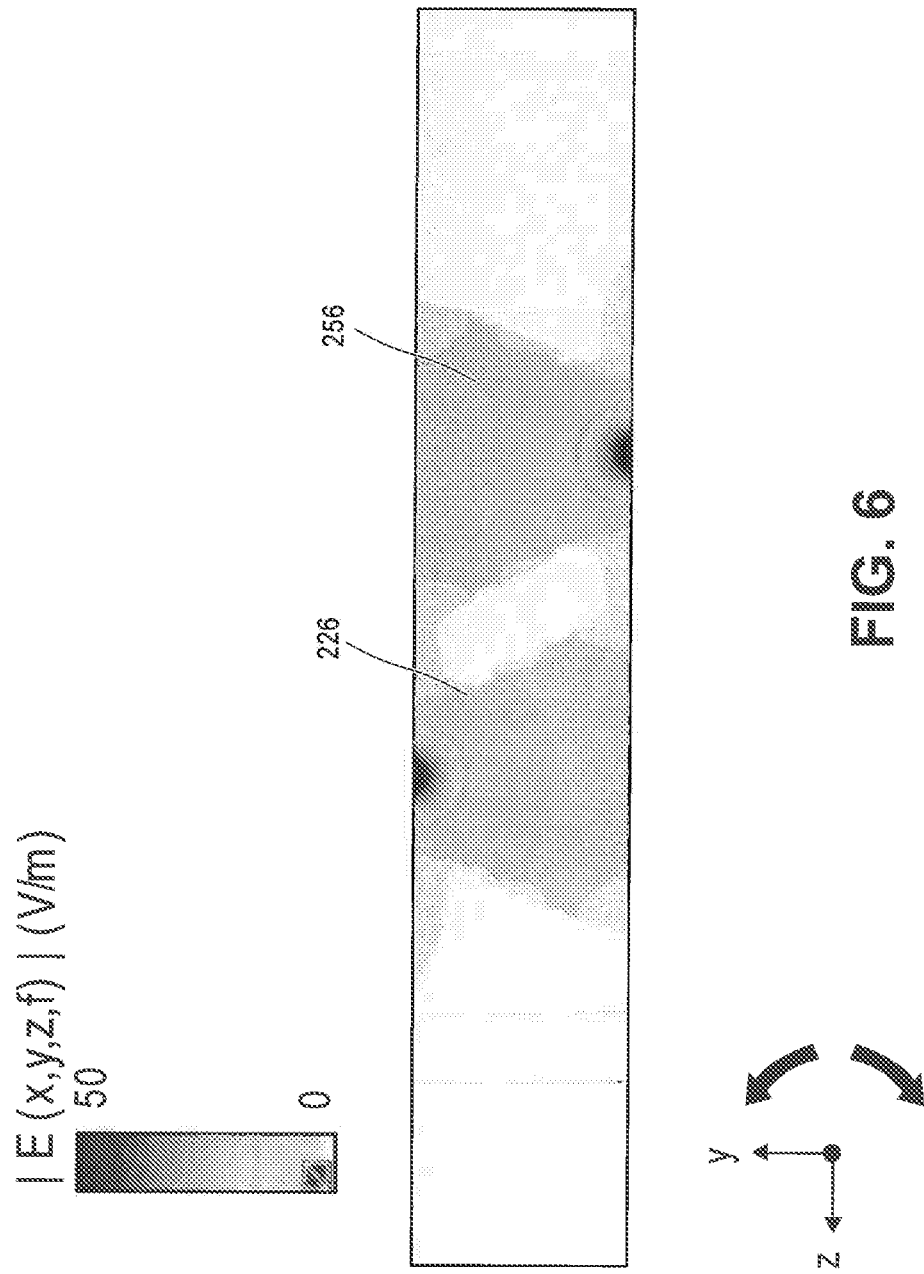
FIG. 6 illustrates a schematic view of electric fields in accordance with embodiments herein.

As a result of the positioning of the openings 232a-232f within the corresponding receiving sections 228 and 230 a flexible lead of an IMD may be positioned in numerous positions within the first electric field 226 (FIG. 6). For example, the flexible lead may be received within the first opening 232a of the first receiving section 228 and the third opening 232f of the second receiving section 230. Alternatively, the lead may be received by the second opening 232b of the first receiving section 228 and the second opening 232e of the second receiving section 230. In yet another example the lead may be received by the third opening 232c of the first receiving section 228 and the second opening 232e of the second receiving section 230. In this manner different sections of the lead are positioned in different proximities to the elongated guiding slot 220 within the first electric field 226 (FIG. 6). The different positions provide additional parameter values or measurements along the lead giving data points, or points of reference to validate the accuracy of the transfer function.

The second electric field generating device 204 of FIGS. 2-4 in this example is essentially a duplicate of the first electric field generating device 202, only facing in an opposite direction. Specifically, the second electric field generating device includes a second housing 236 that includes a first plate 238 in parallel spaced relation to a second plate 240 both secured to a front panel 242 and a back panel 244 to define an interior cavity 246. In one example the first plate 238, second plate 240, front panel 242, and back panel 244 are of one piece construction. Alternatively, each is joined or coupled together through a fastening method such as welding. The first plate 238 and second plate 240 in one example each comprise a metallic material such that when current is run through the plates 238, 240 the first plate presents a first charge, such as in one example a positive charge, while the second plate presents a second charge that is an opposite charge to the charge of the first plate, and in one example a negative charge. In this manner an electric field is generated or formed within the interior cavity 246 in the housing 236 between the first and second parallel plates 238 and 240.

A feed or power source 248 is electrically coupled to the first and second plates 238 and 240. In one example, the power source 248 of the second electric field generating device 204 and the current source 218 of the first electric field generating device 202 are the same. Additionally and alternatively, separate power sources 218 and 248 as illustrated are provided. In one example the power source 248 is a variable current source wherein in the current flowing through the first and second plates 238 and 240 may be varied to vary the amplitude, phase, and frequency of the electric field between the first and second plates 238 and 240. In one example the input power provided to the first electric field generating device 202 and second electric field generating device 204 is scaled to 1 W there is a 180-degree phase difference between the input sources of the devices 202, 204 to provide a phase reversal case. In this manner numerous electric fields may be formed by the second electric field generating device 204. In another example, the current source is constant, and a regulating device or controller controllably alters the current flowing to the first and second plates 238, 240, again to provide numerous electric fields formed by the second electric field generating device 204.

The front panel 242 in one example includes an elongated guiding slot 250 disposed therethrough. Specifically, disposed within the defined interior cavity 246 are a first angled surface 252 and a second angled surface 254. The first angled surface 252 tapers from the first plate 238 to the elongated guiding slot 250 while the second angled surface 254 similarly tapers from the second plate 240 to the elongated guiding slot 250. In this manner the first angled surface 252 and second angled surface 254 taper toward one another with each terminating on either side of the elongated guiding slot 250. As a result of the first angled surface 252 and second angled surface 254, the formed electric field is emitted from the interior cavity 246 defined in the housing 236 through the elongated guiding slot 250 to provide a corresponding second electric field 256 (FIG. 6) proximate to the elongated guiding slot.

A first receiving section 258 and a second receiving section 260 extend from the housing 236. In an example the first receiving section 258 and second receiving section 260 are fan out plates with the second electric field 256 (FIG. 6) formed between the first receiving section 258 and second receiving section 260. In one example the first receiving section 258 and second receiving section 260 extend at an angle from the housing away from the housing 236 and away from a center axis 261 formed through the elongated guiding slot 250. In this manner the first receiving section 258 and second receiving section 260 extend along diverging pathways away from the housing 236. In one example the first receiving section 258 and second receiving section 260 are each of one piece construction with the housing 236. Alternatively, the first receiving section 258 and second receiving section 260 are each mechanically coupled to the housing 236.

The receiving sections 258 and 260 have a plurality of openings 262a-262f where the openings 262a-262f are configured to receive a lead of an IMD. In one example the centers of the first openings 262a and 262d of the receiving sections 258 and 260 are two centimeters from the front panel 242 while the centers of the second openings 262b and 262e are 6 cm from the front panel 242, and the center of the final or third openings 262c and 262f of the receiving sections 258 and 260 are 10 cm from the front panel 242. In this manner, the center of each opening is approximately 4 cm from a next corresponding center of an opening.

As a result of the positioning of the openings 262a-262f within the corresponding receiving sections 258 and 260, a flexible lead of an IMD may be positioned in numerous positions within the second electric field 256 (FIG. 6). For example, the flexible lead may be received within the first opening 262a of the first receiving section 258 and the third opening 262f of the second receiving section 260. Alternatively, the lead may be received by the second opening 262b of the first receiving section 258 and the second opening 262e of the second receiving section 260. In yet another example the lead may be received by the third opening 262c of the first receiving section 258 and the second opening 262e of the second receiving section 260. In this manner different sections of the lead are positioned in different proximities to the elongated guiding slot 250 within the second electric field 256 (FIG. 6). The different positions provide an additional parameter value or measurement along the lead, giving data points, or points of reference to validate the accuracy of the transfer function.

As illustrated with reference to FIG. 2, the first electric field generating device 202 and the second electric field generating device 204 are positioned in close proximity to one another having a predetermined distance between the elongated guiding slot 220 of the first electric field generating device 202 and the elongated guiding slot 250 of the second electric field generating device 204. In one example the pre-determined distance is in a range between 30 cm-100 cm. In one example, as illustrated in FIG. 2, the first electric field generating device 202 is positioned to face in a first direction transverse to the central axis 231 of the first electric field generating device 202 while the second electric field generating device 204 is positioned to face in a second direction opposite to the first direction and transverse to the central axis 261 of the second electric field generating device 204. In this manner, in this example the central axis 231 of the first electric field generating device 202 and the central axis 261 of the second electric field generating device 204 are parallel to one another while the front panel 212 of the first electric field generating device 202 and the front panel 242 of the second electric field generating device 204 similarly are in parallel to one another.

In one example when the first electric field generating device 202 and the second electric field generating device 204 face one another, or have front panels 212 and 242 that are parallel to one another, the first receiving section 228 of the first electric field generating device 202 extends adjacent to and alongside of the first receiving section 258 of the second electric field generating device. In this manner the first electric field generating device 202 and second electric field generating device 204 are positioned in close proximity to one another, and the first electric field 226 (FIG. 6) is positioned in side-by-side relation to the second electric field 256. Specifically, in one example the first and second receiving sections 228 and 230 of the first electric field generating device 202 and the first and second receiving sections 258 and 260 of the second electric field generating device 204 align with one another such that first openings 232a, 232d, 262a, and 262d all align. In this manner an unbent, straight lead may be disposed through and received by each of the first openings 232a, 232d, 262a, 262d such that the entire section of the lead within the first electric field 226 (FIG. 6) and second electric field 256 (FIG. 6) extends parallel to the front panels 212 and 242 of the corresponding electric field generating devices 202 and 204. In an example, the lead of the IMD may similarly be placed through the second openings 232b, 232e, 262b, 262e, or alternatively through the third openings 232c, 232f, 262c, 262f to extend parallel to the front panels 212 and 242 of the corresponding electric field generating devices 202 and 204.

Figure 5:
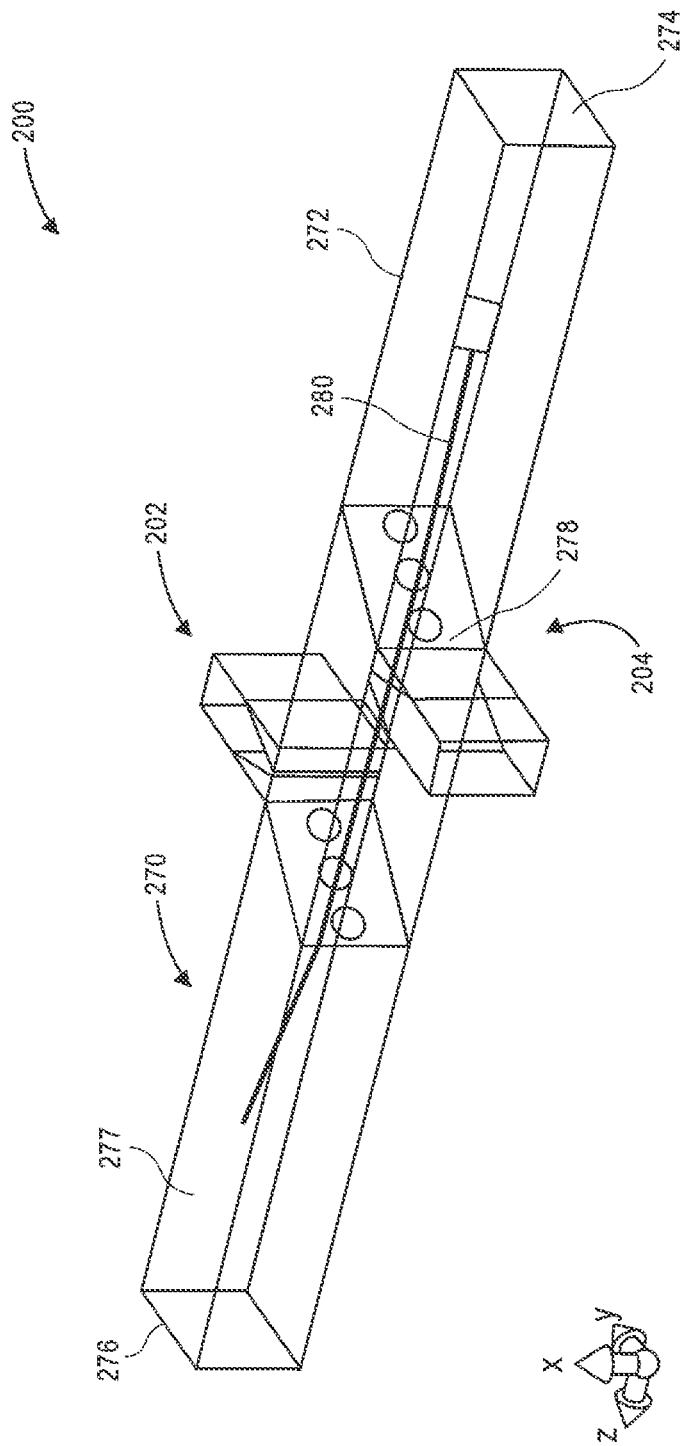
FIG. 5 illustrates a perspective view of a validation system operated in accordance with embodiments herein.

FIG. 5 illustrates the validation system 200 including the first electric field generating device 202 and second electric field generating device 204 within a phantom 270 used to assist in validating transfer functions associated with the lead of an IMD. The phantom in one example is a tissue stimulating medium. Optionally, the electric field generating device 202 and second electric field generating device 204 are partially within the phantom 270. Alternatively, the electric field generating device 202 and second electric field generating device 204 are in air and not within a phantom. FIG. 6 illustrates example electric fields 226, 256 generated as a result of the validation system 200 being used in association with the phantom 270. The phantom 270 includes a housing 272 that extends from a first end 274 to a second end 276. In one example the housing 272 is at least one-hundred and twenty (120) cm in length from the first end 274 to the second end 276 to accommodate a lead of at least a hundred (100) cm. Disposed within the housing is a substrate 277 that is formed to replicate tissues and materials of the human body through which the lead will extend when implanted in a patient. In one example the phantom 270 is a tissue simulating saline or gel disposed within a rectangular tank.

The housing 272 in one example includes slotted openings 278 for receiving the receiving sections 228, 230, 258, 260 of each electric field generating device 202, 204. In this manner the lead of the IMD may be inserted through the phantom material and the receiving sections while the housings 206 and 236 remain outside of the phantom 270 to prevent the phantom material from leaking into the housings 206 and 236. Alternatively, the housings 206 and 236 are placed into the phantom 270 and sealed to prevent leakage of saline, gel, and the like into the housings 206 and 236.

FIGS. 7-15 illustrate top view examples of leads 280 of an IMD placed in the phantom 270 of FIG. 5 along with accompanying graphs that illustrate the tangential electric field effect measured in volts per meter (y-axis) over the distance along the lead in millimeters (x-axis), and the tangential electric field effect measured in degrees (y-axis)

over the distance along the lead in millimeters (x-axis). For the leads 280 illustrated, an input frequency of 128 MHz and a 58 cm lead 280 is provided. While the example embodiments utilize a 58 cm lead 280 and an input frequency of 128 MHz, in other examples different sized leads 280 are provided with different input frequencies. Specifically, FIGS. 7-15 are only meant to illustrate how the validation system 200 may be utilized to provide numerous different positions of the lead 280 in the electric fields 226 and 256 generated by the validation system 200 and the information that may be gathered utilizing the validation system 200. Additionally, while the example embodiment of FIGS. 1-6 only illustrates the use of two electric field generating devices 202, 204, in other example embodiments more than two electric field generating devices are utilized. In all, for the leads 280 illustrated, the sections 282 and 284 are presented in different positions relative to one another with the first electric field 226 and the second electric field 256 resulting in different outputs 286, 288, 290, 292, 294, and 296 in each graph.

Figure 7:
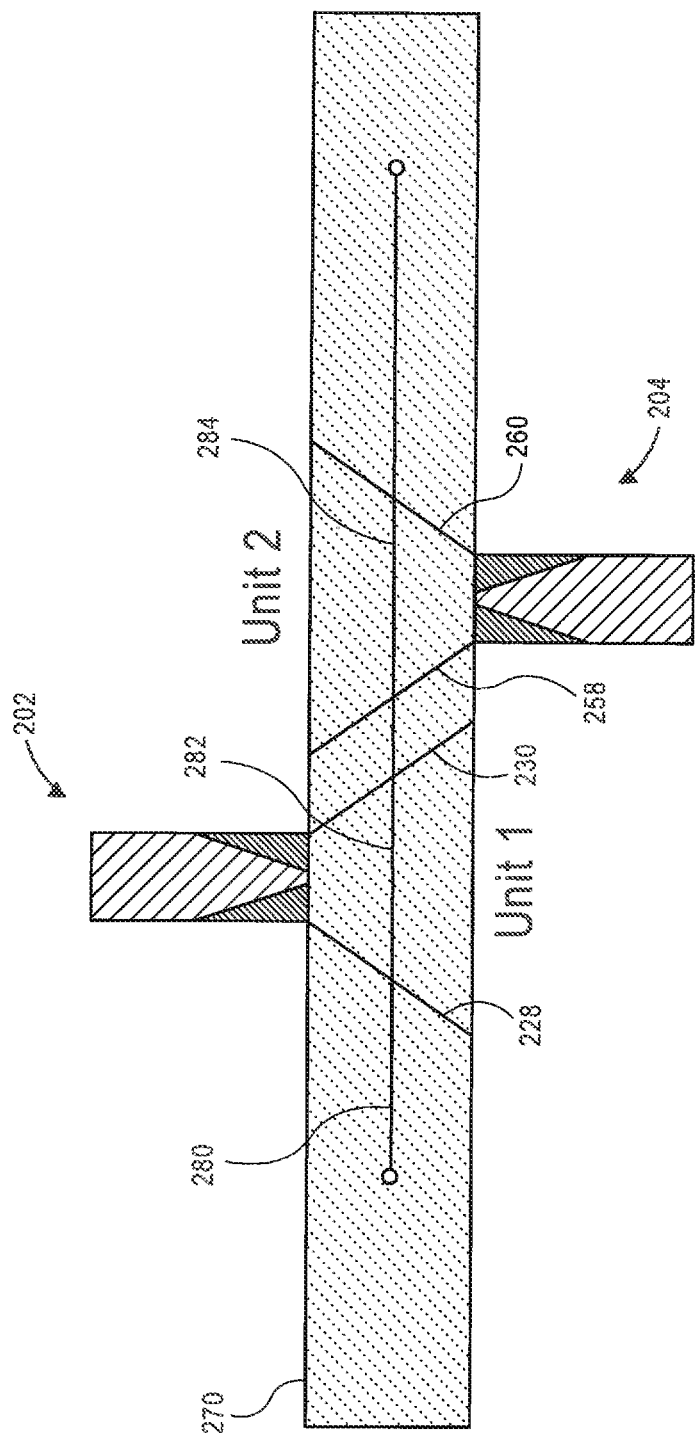
FIG. 7 illustrates a top plan view of a validation system operated in accordance with embodiments herein.
Figure 8:
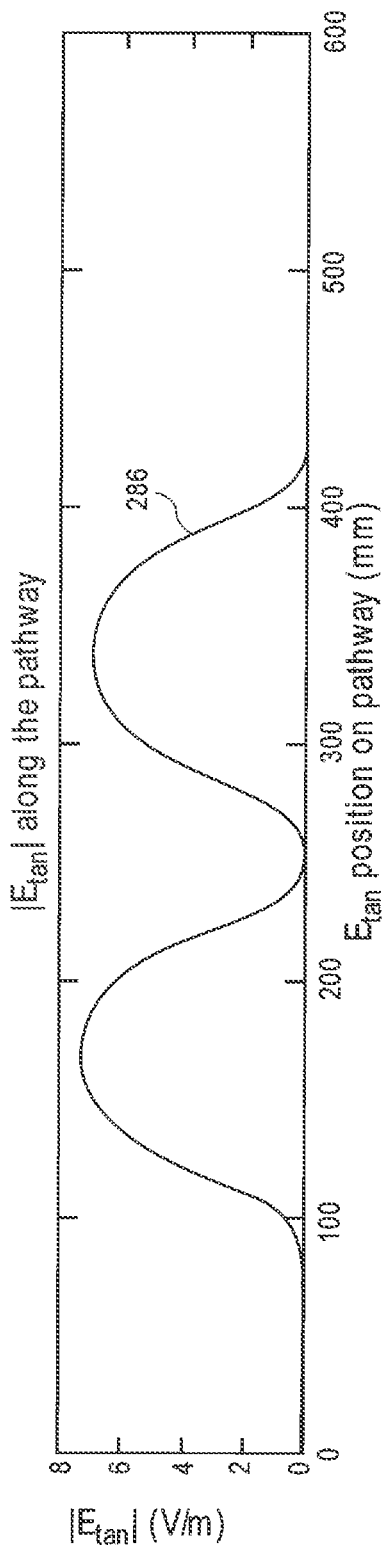
FIG. 8 illustrates a graph of volts per meter over a distance along a lead in accordance with embodiments herein.
Figure 9:
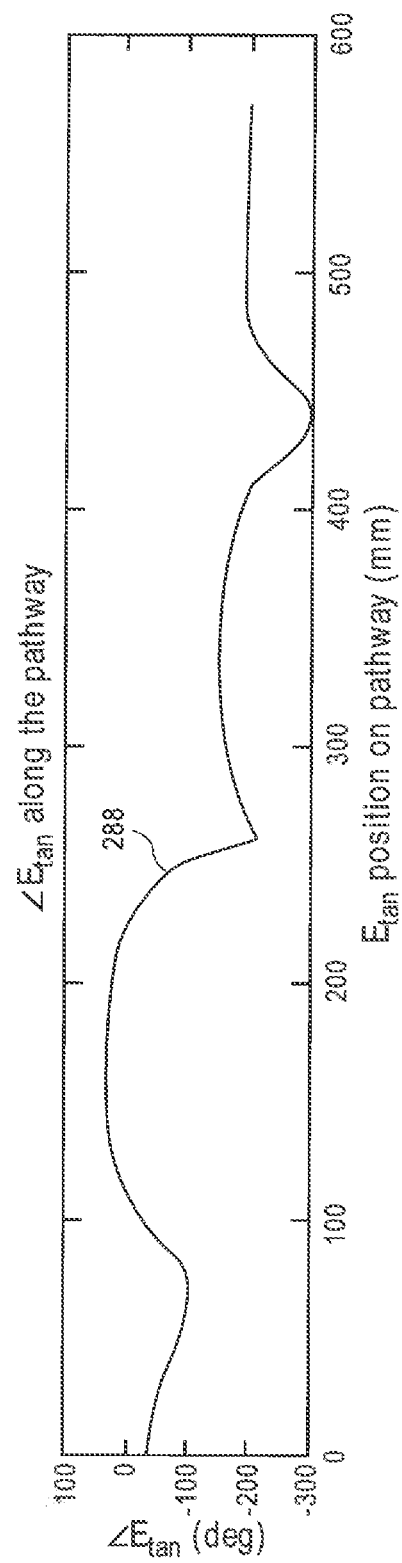
FIG. 9 illustrates a graph of degrees over a distance along the lead in accordance with embodiments herein.

FIGS. 7-9 illustrate a lead 280 that includes a first section 282 that extends through the second opening 232b of the first receiving section 228 of the first electric field generating device 202, to the second opening 232e of the second receiving section 230 of the first electric field generating device 202. The lead 280 then extends through the second opening 232e of the second receiving section 230 of the first electric field generating device 202 and between the second receiving section 230 of the first electric field generating device 202 to the first receiving section 258 of the second electric field generating device 204. The second section 284 of the lead 280 then extends from the second opening 262b in the first receiving section 258 of the second electric field generating device 204 to the second opening 262e in the second receiving section 260 of the second electric field generating device 204. The lead then extends through the second opening 262e in the second receiving section 260 of the second electric field generating device.

As illustrated in the graph of FIG. 8, as the first tangential electric field is measured across the first section 282 of the lead, the output 286 increases from the second opening 232b to a local maximum when placed directly in front of the elongated guiding slot 220. The output 286 then decreases back to local minimum at the portion of the lead between the second receiving section 230 of the first electric field generating device 202 and the first receiving section 258 of the second electric field generating device 204. From this local minimum, the tangential electric field increases in tangential electric field strength to another local maximum when the second section 284 is in front of the elongated guiding slot 250 of the second electric field generating device 204. The tangential electric field strength then decreases along the second section 284 of the lead 280 until reaching another local minimum after extending through the second opening 262e of the second receiving section 260 of the second electric field generating device 204. In particular, because the lead is positioned in the second openings 232b, 232e, 262b, 262e of each receiving section 228, 230, 258, 260, the lead is straight, or unbent, and the symmetrical wave results.

FIG. 9 illustrates the change in tangent electric field in degrees when there is a 180-degree phase difference between the first electric field generating device 202 and second electric field generating device 204, thus providing phase reversal. The first section 282 of the lead 280 increases gradually and then remains relatively constant while in the first electric field 226 and then decreases to a second relatively constant degree on the second section 284 of the lead 280 in the second electric field 256. Thus, the straight lead 280 provides constant results through the first and second electric fields 226, 256.

Figure 10:
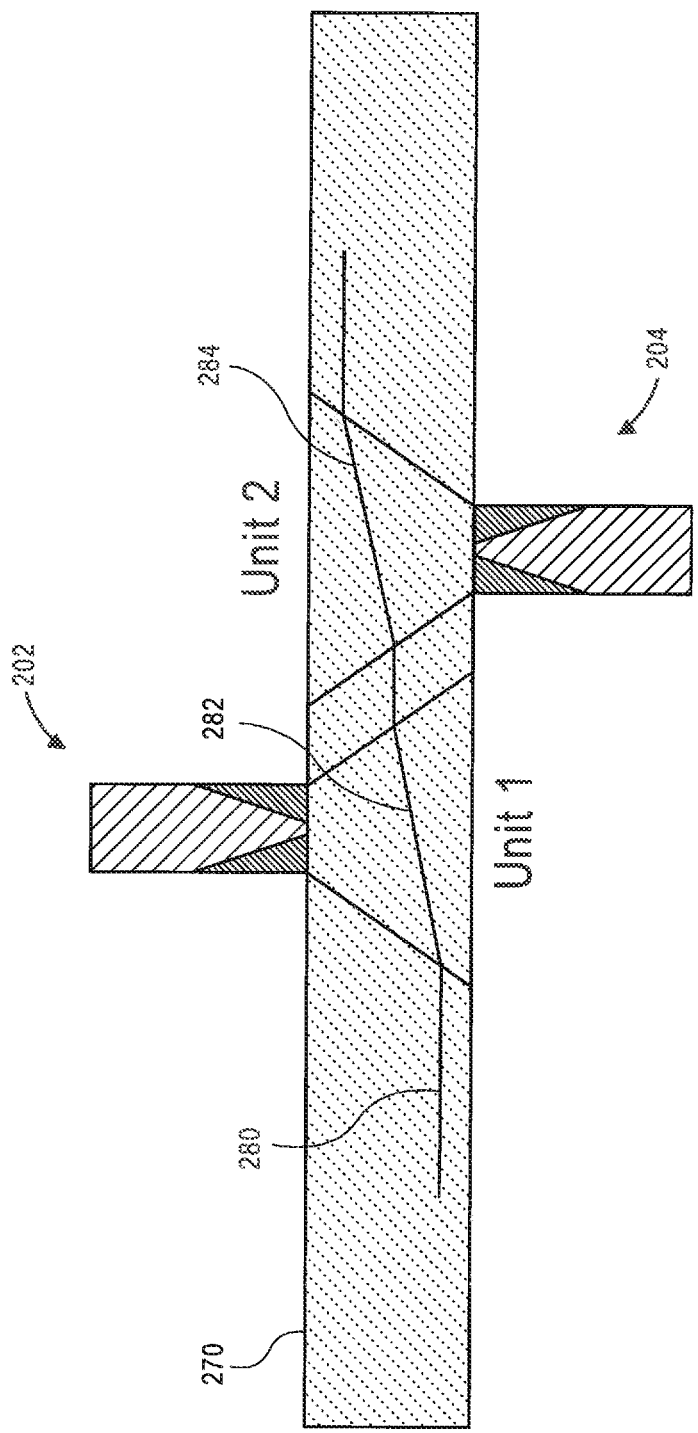
FIG. 10 illustrates a top plan view of a validation system operated in accordance with embodiments herein.

FIG. 10 illustrates an example wherein the same lead 280 is now bent and thus disposed through different openings of the receiving sections 228, 230, 258, 260. In this example, the first section 282 of the lead 280 extends from the third opening 232c of the first receiving section 228 of the first electric field generating device 202 to the second opening 232e of the second receiving section 230 of the first electric field generating device 202. The lead then extends to the second opening 262b of the first receiving section 258 of the second electric field generating device 204. The second section 284 of the lead 280 extends from the second opening 262b of the first receiving section 258 of the second electric field generating device 204 to the third opening 262f of the second receiving section 260 of the second electric field generating device 204. Therefore, in this example both the first section 282 and second section 284 of the lead 280 are angled in relation to each front panel 212 and 242 respectfully. Additionally, the sections 282 and 284 are angled in a different manner. Thus, the validation system can be utilized to determine the effect of the same strength electric field with the lead 280 at a variety of positions, increasing the number of readings and thus data points received by the validation system during testing. Therefore, efficiencies are improved while the need for an RF coil is eliminated, reducing costs.

Figure 11:
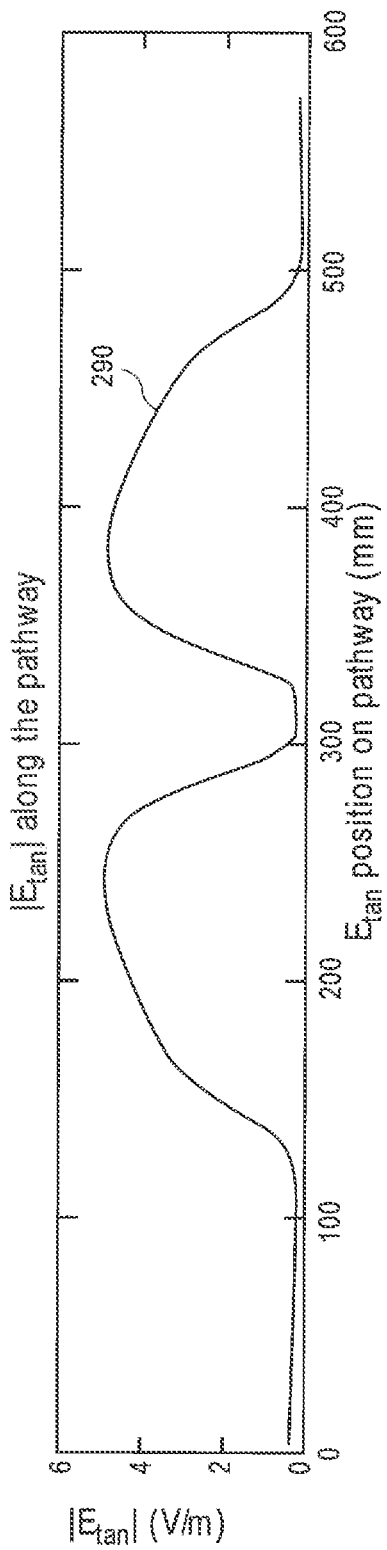
FIG. 11 illustrates a graph of volts per meter over a distance along a lead in accordance with embodiments herein.
Figure 12:
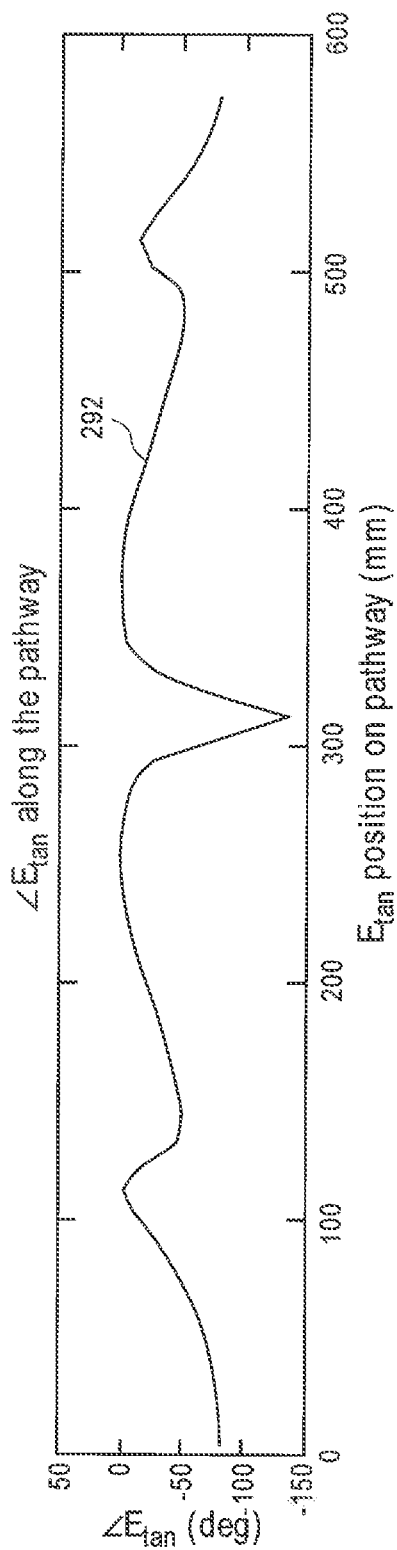
FIG. 12 illustrates a graph of degrees over a distance along the lead in accordance with embodiments herein.

FIGS. 11 and 12 are graphs of the effect of the electric fields along the length of the lead 280. For each graph, similar to the graphs of FIGS. 8-9 the positioning of the lead 280 effects the electric fields along the length of the lead 280. Thus, such reading, or parameter value, may be compared to expected parameter values derived from a transfer function in order to validate the transfer function.

Figure 13:
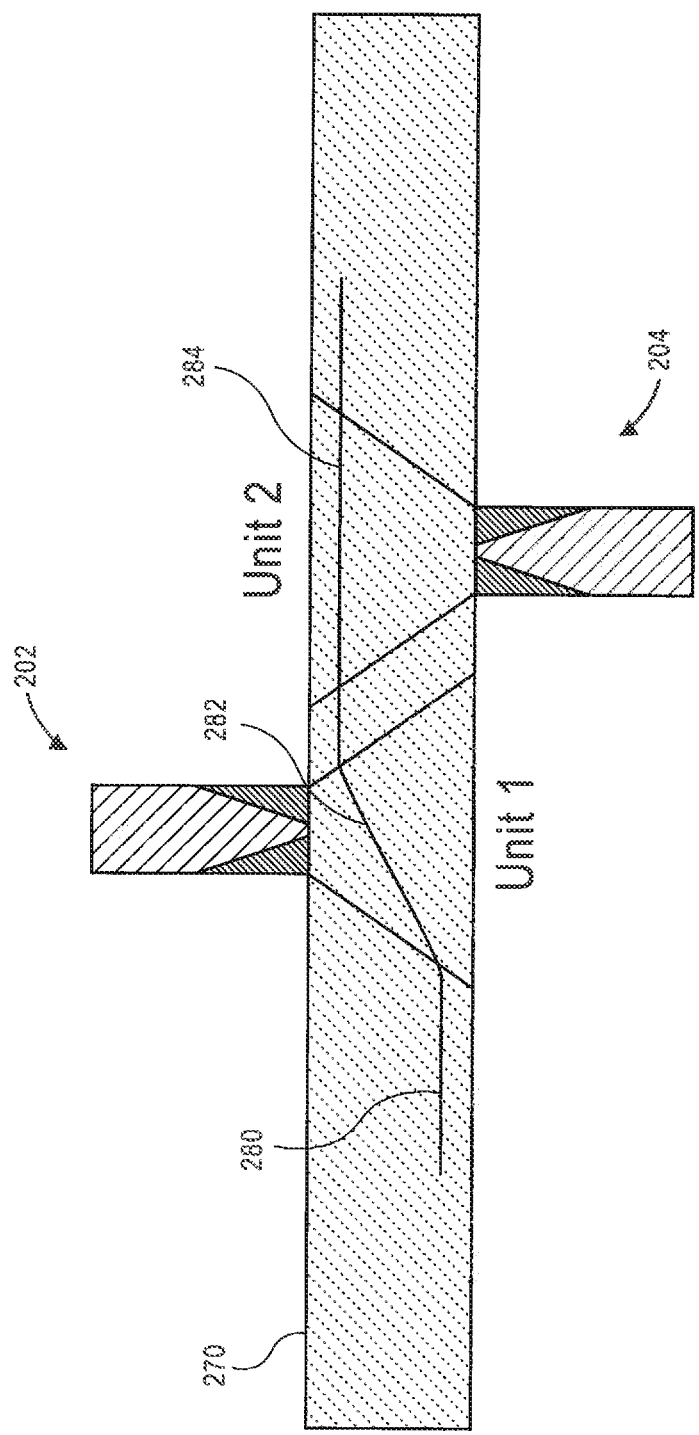
FIG. 13 illustrates a top plan view of a validation system operated in accordance with embodiments herein.
Figure 14:
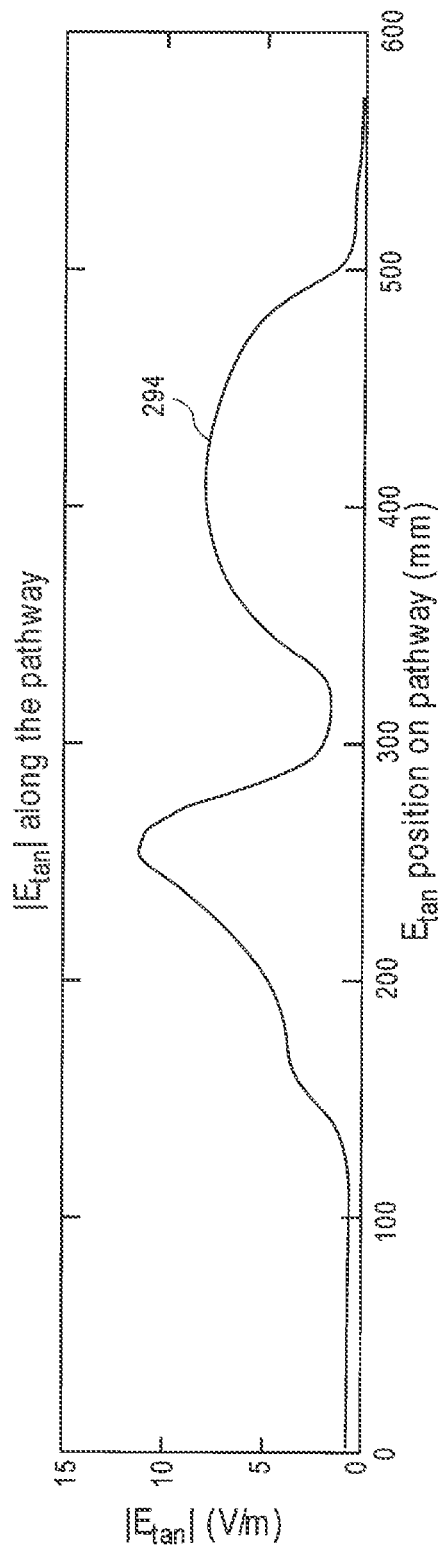
FIG. 14 illustrates a graph of volts per meter over a distance along a lead in accordance with embodiments herein.
Figure 15:
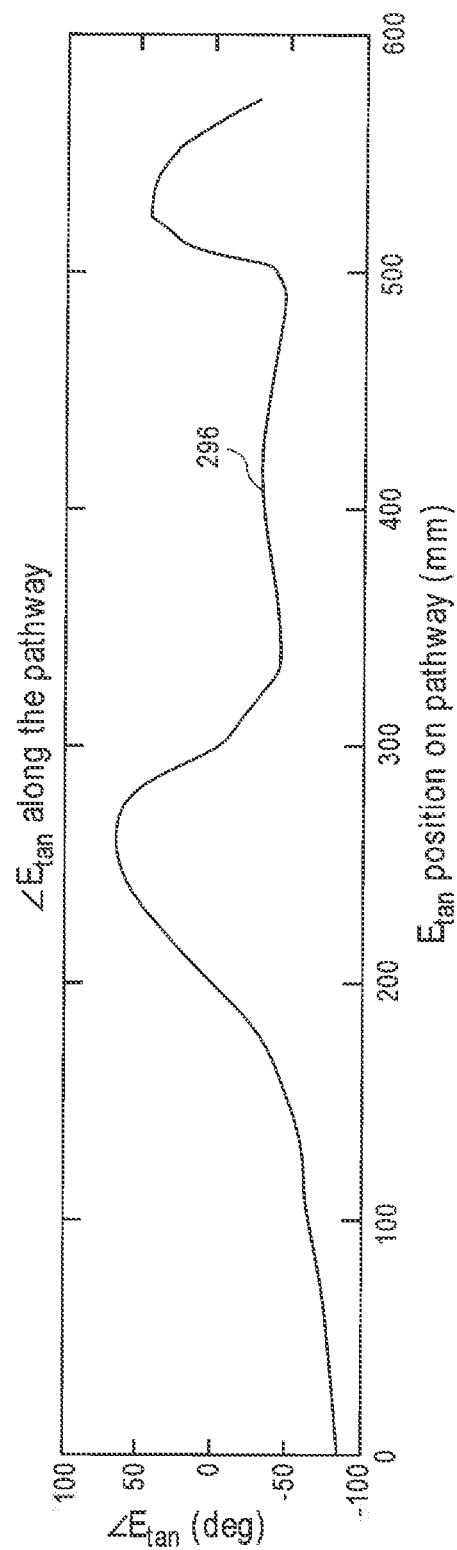
FIG. 15 illustrates a graph of degrees over a distance along the lead in accordance with embodiments herein.

FIG. 13 illustrates a final example of the positioning of the lead 280 within the validation system 200. In this example the first section 282 of the lead 280 extends from third opening 232c of the first receiving section 228 of the first electric field generating device 202 to the first opening 232d of the second receiving section 230 of the first electric field generating device 202. The lead then extends to the third opening 262c of the first receiving section 258 of the second electric field generating device 204. Meanwhile, the second section 284 of the lead 280 extends from the third opening 262c of the first receiving section 258 of the second electric field generating device 204 to the third opening 262f of the second receiving section 260 of the second electric field generating device 204. In this manner the first section 282 is angled related to the front panel 212 of the first electric field generating device 202 wherein the second section 284 is parallel to the front panel 242 of the second electric field generating device 204. Consequently, numerous different readings, and combinations with regard to positioning within an electric field is provided, increasing the amount of data that is received at one time from the validation system 200. Thus, again, efficiencies are improved while cost is reduced as a result of eliminating the use of an RF coil during the validation process.

FIGS. 14 and 15 again illustrate graphs that illustrate the effect of the electric fields along the length of the lead 280 in relation to the positioning of the lead illustrated in FIG. 13. For each graph, similar to the graphs of FIGS. 8-9 and 11-12, the positioning of the lead 280 effects the electric fields along the length of the lead 280. Thus, such reading may be compared to expected reading derived from a transfer function in order to validate the transfer function.

In all, the FIGS. 7-15 illustrate that tangential electric field exposure can be changed by 1) manipulating the signal magnitude and phase of the exposure units, and 2) passing the lead through different openings to change lead position. Additionally or alternatively, additional variable parameters can be utilized to create unique tangential electric fields to a lead (Etans). In one example the entire lead is moved horizontally along the longest axis of the phantom 270. By moving the lead along the longest axis of the phantom 270, the tangential electric field patterns with respect to the entire lead length are changed, thus creating a set of linearly independent tangential electric field vectors along the pathway.

In each instance, electric field vectors are determined utilizing this methodology. In one example a matrix may be utilized to ensure duplication of data points are avoided. In one example twenty-five (25) tangential electric field vectors ($E_{tan}(i, I)$, i=1, 2, . . . 25, 0≤/≤58 cm) may be generated using the methods described above. These tangential electric field vectors in an example are directed toward a lead 280 that has a 58 cm pathway length with 1 cm spatial resolution. To verify the linear independent property of these Etans, a matrix is provided with tangential electric field vectors as matrix rows with each Etans being unique such that duplicates are discarded to ensure the correct number of Etans vectors are determined. It should be noted that the number of unique Etans the proposed system can generate is far more than 25, and for a specific lead model, the actual Etans are designed based on signal-to-noise ratio (SNR) as well. Therefore, the Etan vectors are arranged to be utilized to validate a transfer function.

FIGS. 16-20 illustrate numerous example validation systems used to validate the safety of a medical device such as an implantable device having a lead when exposed to magnetic resonance imaging fields. The example validation systems utilize electric generating devices used in association with a lead of an IMD to vary position of the lead within numerous electric fields in order to create readings similar as described above. With the validation systems of FIGS. 16-20, the electric generating devices vary; however, the advantages and methodology remain the same for the individual validation systems of FIGS. 16-20.

Figure 16:
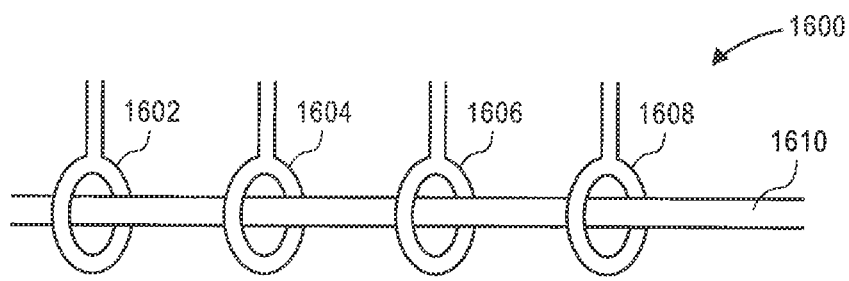
FIG. 16 illustrates a schematic view of a validation system operated in accordance with embodiments herein.

FIG. 16 illustrates a schematic diagram of a validation system 1600 that includes a first electric field generating device 1602, a second electric field generating device 1604, a third electric field generating device 1606, and a fourth electric field generating device 1608. Each electric field generating device 1602, 1604, 1606, and 1608 may vary the electric field amplitude, phase, and frequency of the electric field. Each electric field generating device 1602, 1604, 1606, and 1608 in this example embodiment is a ring or coil element. Thus, in this example a first coil, second coil, third coil, and fourth coil are provided in side-by-side relation and are aligned with one another. In one example the ring or coil element is a toroidal coil. In another example the ring element is a solenoid coil. Thus, for each electric field generating device 1602, 1604, 1606, and 1608 an electric field is generated within each coil. Thus, a first electric field, second electric field, third electric field, and fourth electric field are provided. A lead 1610 is then disposed through each electric field generated by each electric field generating device 1602, 1604, 1606, and 1608. In one example each electric field generating device 1602, 1604, 1606, and 1608 is aligned such that the lead 1610 may be straight, or unbent, and disposed through each of the electric field generating devices 1602, 1604, 1606, and 1608. Consequently, numerous readings are simultaneously taken regarding how the lead 1610 is affected by the electric field formed by each electric field generating device 1602, 1604, 1606, and 1608.

Figure 17:
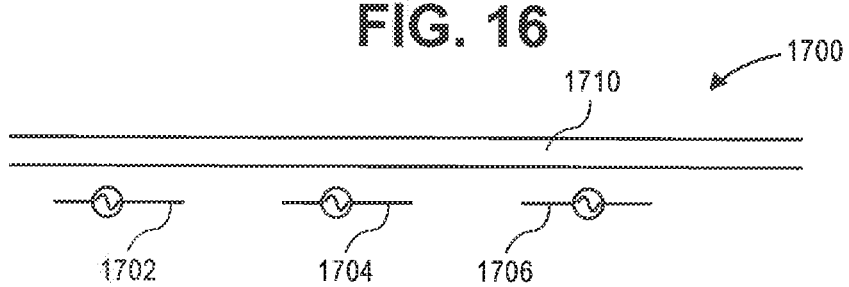
FIG. 17 illustrates a schematic view of a validation system operated in accordance with embodiments herein.

FIG. 17 illustrates a validation system 1700 that includes a first electric field generating device 1702, a second electric field generating device 1704, and a third electric field generating device 1706. Each electric field generating device 1702, 1704, and 1706 may vary the electric field amplitude, phase, and frequency of the electric field. In this example embodiment each electric field generating device 1702, 1704, and 1706 includes a dipole that each generates an electric field such that three side-by-side-by-side electric field are formed, similar to those generated in relation to validation system 200 of FIG. 2. Therefore, in this example the lead 1710 is positioned adjacent each dipole in each formed electric field. Therefore, again, numerous readings are simultaneously taken regarding how the lead 1710 is affected by the electric field formed by each electric field generating device 1702, 1704, and 1706.

Figure 18:
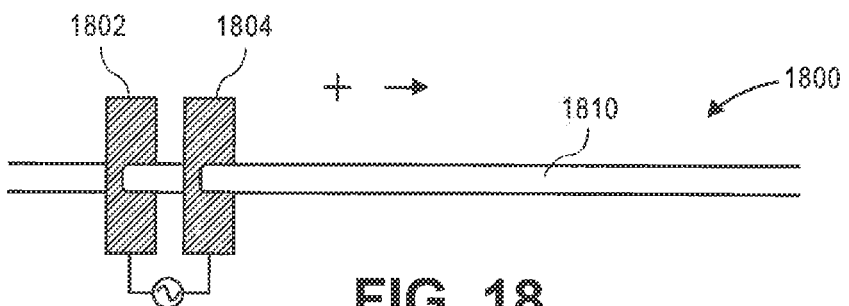
FIG. 18 illustrates a schematic view of a validation system operated in accordance with embodiments herein.

FIG. 18 illustrates a validation system 1800 that includes a first electric field generating device 1802, and a second electric field generating device 1804. Each electric field generating device 1802 and 1804 may vary the electric field amplitude, phase, and frequency of the electric field. In this example embodiment each electric field generating device 1802, and 1804 includes parallel plates with an opening therethrough. The lead 1810 is disposed through the openings within each pair of parallel plates to expose the lead 1810 to each electric field formed by each pair or set of parallel plates. Therefore, again, numerous readings are simultaneously taken regarding how the lead 1810 is affected by the electric field formed by each electric field generating device 1802, and 1804.

Figure 19:
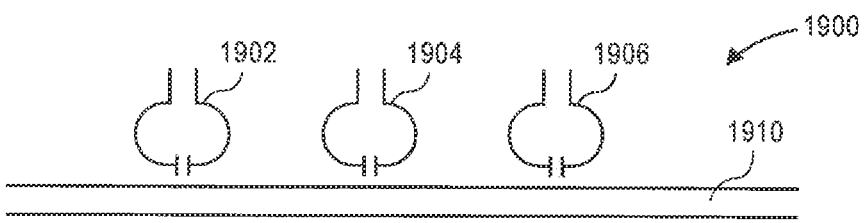
FIG. 19 illustrates a schematic view of a validation system operated in accordance with embodiments herein.

FIG. 19 illustrates a validation system 1900 that includes a first electric field generating device 1902, a second electric field generating device 1904, and a third electric field generating device 1906. Each electric field generating device 1902, 1904, and 1906 may vary the electric field amplitude, phase, and frequency of the electric field. In this example embodiment each electric field generating device 1902, 1904, and 1906 includes a set of parallel plates that generate an electric field. Instead of being disposed through an opening within the plates, in this example the lead 1910 is place adjacent or in close proximity to each set of parallel plates such that the lead 1910 is disposed through each electric field formed by each electric field generating device 1902, 1904, and 1906. Therefore, again, numerous readings are simultaneously taken regarding how the lead 1910 is affected by the electric field formed by each electric field generating device 1902, 1904, and 1906.

Figure 20:
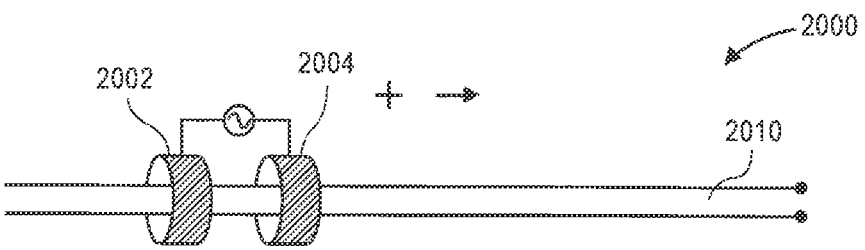
FIG. 20 illustrates a schematic view of a validation system operated in accordance with embodiments herein.

FIG. 20 illustrates a validation system 2000 that includes a first electric field generating device 2002, and a second electric field generating device 2004. Each electric field generating device 2002 and 2004 may vary the electric field amplitude, phase, and frequency of the electric field. In this example embodiment each electric field generating device 2002, and 2004 is a metal ring that receives current to form an electric field therein. The lead 2010 is then disposed through each ring, placing the lead 2010 in each electric field formed by each electric field generating device 2002 and 2004. Therefore, again, numerous readings are simultaneously taken regarding how the lead 2010 is affected by the electric field formed by each electric field generating device 2002 and 2004.

Process for Validating Transfer Functions

In order to predict heating of an active IMD lead as a result of MRI use, or radio-frequency (RF) heating, or in order to predict voltage on an active IMD lead as a result of MRI use, or RF header voltage, a transfer function, which relates to the incident electric field tangential to a lead (Etan) to the output which is heating (temperature rise) or varying voltage, needs to be determined first. The results of the transfer function are then compared to measurements taken of the active IMD using validation systems as described above in order to validate the safety of an implantable lead when exposed to magnetic resonance imaging fields.

Figure 21:
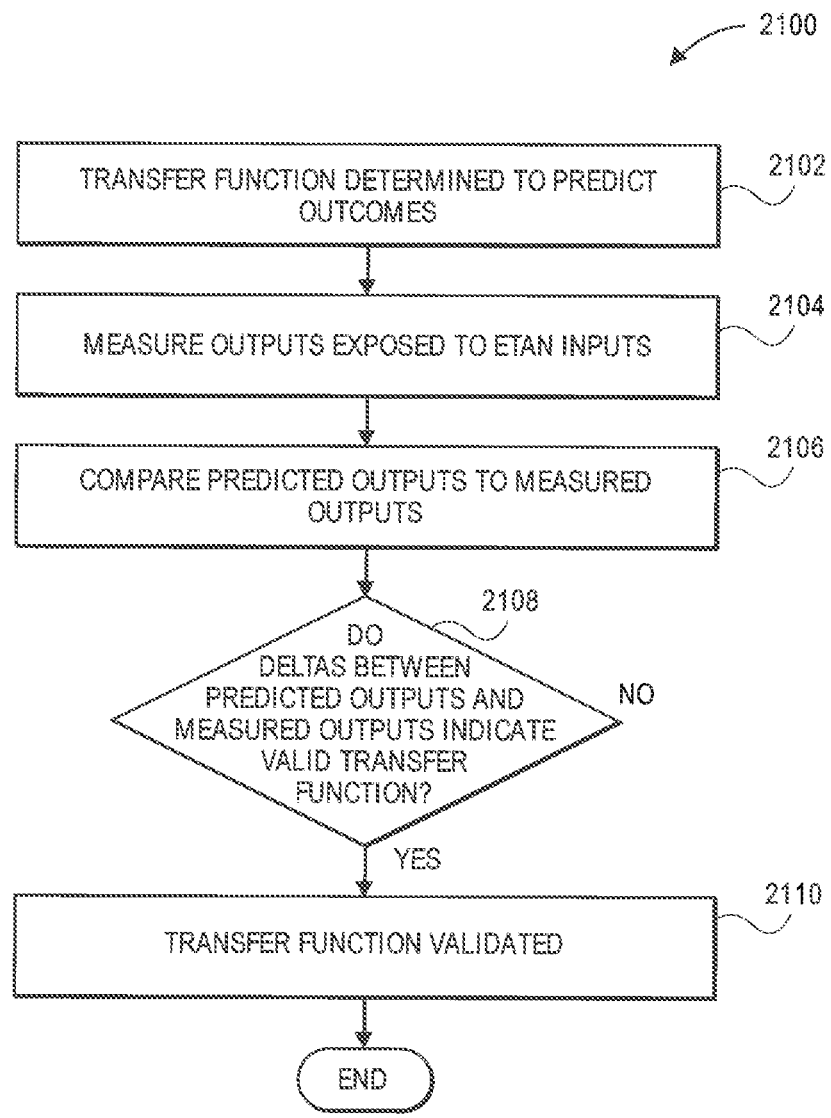
FIG. 21 illustrates a flow block diagram of a method of validating at least one transfer function in accordance with embodiments herein.

FIG. 21 illustrates a method 2100 for validating transfer functions. The method in one example is performed by one or more processors that execute instructions to perform the method provided. In one example, the one or more processors are the one or more processors 124 of the validation system of FIG. 1. In example embodiments, the one or more processors are coupled to at least one of an MRI device, an IMD, and/or an external instrument (EI) such as a heart monitor, and the like. Specifically, coupling to the device includes remote coupling through over the air communications, or coupled as part of a computing device of the device, instrument, or monitor.

At 2102 a transfer function is determined for a medical device such as an IMD to provide predicted parameter values related to the medical device. In particular, the transfer function is defined to predict a safety characteristic of the medical device when in the presence of an MRI field. In one example, the medical device is an IMD and the safety characteristic is the resultant temperature on the IMD as a result of the field. In another example the safety characteristic is the voltage on the IMD caused by the MRI field.

In one example a transfer function is determined for a different magnetic field strengths. In one example the field strength is 0.2 Tesla (T). In another example the field strength is 7 T. In another example the field strength is in a range between 0.2 T and 7 T. In one example, the transfer function is determined for a 2 T magnetic field while and determined for a 5 T magnetic field. Consequently, the outputs are predicted utilizing the determined transfer function. In one example a tangential electric field (Etan), including the magnitude and phase are inputted into the transfer function to provide the output prediction along the lead. In one example the output prediction is a parameter value of the lead, including temperature at a given location on the lead. In another example the output prediction is a parameter value of the lead, including voltage at a given location along the lead. In yet another example, the output prediction is a parameter value of the lead that includes both the temperature and voltage at a given location along the lead. In yet another example the output prediction is a parameter value of at least one of power, e-field, h-field, medical device current, or the like.

At 2104, a medical device such as an IMD is exposed to Etan inputs and one or more processors of the system obtain measured parameter values from the medical device, the measured parameter values indicative of the safety characteristic of the medical device when exposed to the first and second electric fields. In one example the Etan inputs are provided utilizing one of the validation systems illustrated and described in relation to FIGS. 1-20. In another example, the measured outputs are determined using the methodology described in relation to FIG. 22. In one example, the measured output is the temperature at any given point along the lead. In another example the measured output is the incident voltage at any given point I of a medical device. Thus, measurements are provided during, or as a result of placement of the lead of the IMD in the Etans.

At 2106, one or more processors of the system compare the measured parameter values to the predicted parameter values determined at 2102. In one example, the comparison is provided by one or more processors coupled to the device or monitor that detects the measured parameter values. This includes a validation system, and/or a device remote to the validation system that has a communication path to receive the measured parameter values. In one example the device remote to the validation system is in communication with monitors the detect the measured parameter values. In another example the device remote to the validation system is in communication with and receives information from a memory of the validation system. In one example the comparison is made by placing the measured parameter values next to the predicted parameter values determined by the transfer function. In one example, a difference associated with each result comparison is also provided. In another example the measured parameter values and predicted parameter values are plotted on the same graph together to provide a visual representation of the difference along with graph parameters such as slope, peak-to-to value and the like. Such results, including side-by-side comparisons and graphs may be displayed on a display for use by a test operator.

At 2108, the one or more processors make a determination regarding whether a delta, or difference, between the measured parameter values and predicted parameter values indicate a valid transfer function is provided. In one example the validity is based on a single measurement or point, such that, even if all other measured parameter values have no difference, if one measurement is less than or greater than a predetermined value of a given measurement parameter value, the transfer function is determined to be invalid. In yet another example, the difference is associated with a parameter of a graph generated as a result of the transfer function compared to the same parameter of a graph generated as a result of the measured parameter values. In yet another example an algorithm is utilized to determine if the differences in measured parameter values compared to predicted parameter values result in an invalid transfer function. Specifically, a weight may be assigned to different measured parameter values depending on variables resulting from taking the measurements, and the like as part of an algorithm in determining if a threshold value has been exceeded.

As another example, both the measurement and the transfer function model prediction is utilized, with both the measurement uncertainty and transfer function model uncertainty combined into the validation criterion. Therefore, the transfer function validation acceptance criterion reads that the error between the measurement and predictions is within the combined measurement and transfer function model uncertainty.

In these manners, numerous methodologies may be utilized to determine if the transfer function is validated utilizing the measurements provided. If at 2108, the transfer function is not validated, a new transfer function must be determined.

At 2110, if the one or more processors make a determination at 2108 that the transfer function is validated then the transfer function is utilized to predict a safety characteristic of the medical device when in the presence of an MRI field. In one example, the safety characteristic is voltage on an IMD, and in another example the safety characteristic is temperature of the IMD caused by the MRI field. Therefore, by utilizing the validation systems as provided herein, an IMD may be validated for use. Such validation systems allow for efficient, cost effective, methods for validating an IMD.

Figure 22:
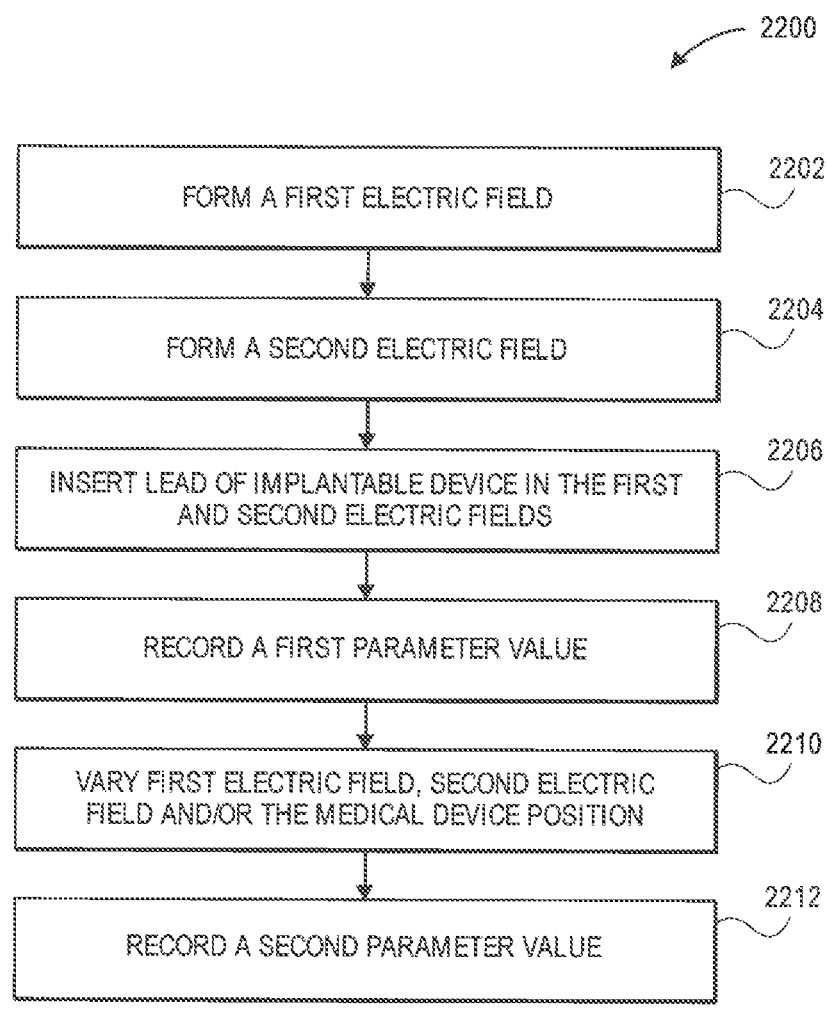
FIG. 22 illustrates a flow block diagram of a method of utilizing a validation system in accordance with embodiments herein.

FIG. 22 illustrates a method 2200 for utilizing a validation system in order to generate measured parameter values utilizing Etan inputs. In one example, this method is utilized to generate measured parameter values at 2104 in order to validate a transfer function as provided in method 2100.

At 2202, a first electric field is formed with a first electric field generating device. In one example the first electric field generating device is the first electric field generating device 202 described in detail in relation to FIGS. 2-15. In another example the first electric field generating device is any of the first electric field generating devices 1602, 1702, 1802, 1902, or 2002 of FIGS. 16-20. In an example, a first electric field generating device is configured to emit the first electric field at a first opening. In yet another example, a first electric field generating device is configured to emit the first electric field within a ring element. In another example, a first electric field generating device is configured to emit the first electric field in proximity to parallel plates.

At 2204, a second electric field is formed with a second electric field generating device. In one example the second electric field generating device is the second electric field generating device 204 described in detail in relation to FIGS. 2-15. In another example the second electric field generating device is any of the second electric field generating devices 1604, 1704, 1804, 1904, or 2004 of FIGS. 16-20. In an example, a second electric field generating device is configured to emit the first electric field at a first opening. In yet another example, a first electric field generating device is configured to emit the first electric field within a ring element. In another example, a first electric field generating device is configured to emit the first electric field in proximity to parallel plates.

At 2206, a lead of an implantable medical device is inserted into the first and second electric field at a first position. In one example the lead is the lead 280 described in detail in relation to FIGS. 2-15. In another example the lead one of any of the leads 1610, 1710, 1810, 1910, or 2010 described in relation to FIGS. 16-20. In an example, at least a section of the first electric field generating device and at least a section of the second electric field generating device are disposed within a tissue simulating saline or gel disposed within a housing such as a rectangular tank. In this manner, the first electric field and second electric field are formed in the tissue simulating substance and the lead is also disposed within the tissue simulating substance to provide more accurate measurements. In one example the lead is disposed through openings in receiving sections of the electric field generating devices. In an example, the first position results in a first section of the lead to be parallel to a front panel of the first electric field generating device while a second section of the lead is angled compared to a front panel of the second electric field generating device. Alternatively, in the first position both the first and second sections of a lead are parallel to the front panel of each of the first and second electric field generating devices. Again, alternatively, in the first position the first section of the lead is angled to the front panel of the first electric field generating device and the second section of the lead is angled to the front panel of the second electric field generating device. In each instance, the first and second sections of the lead are positioned at differing predetermined distances from an electric field generating device and thus are presented in different positions within the first electric field and second electric field. In one example the first and second sections of the lead are positioned at differing predetermined distances from an opening of an electric field generating device.

At 2208, a first measured parameter value of the lead in the first electric field and second electric field in the first position is recorded. In one example the first measure parameter value is the temperature of the lead that is measured at predetermined positions along the lead within each electric field. In another example the first measured parameter value is the voltage of the lead that again is measured at predetermined positions along the lead within each electric field. In one example the first measured parameter value is measured directly with a sensor such as a temperature sensor or voltage sensor. Alternatively, a measurement of another measured parameter is detected or measured, and an algorithm is utilized by one or more processors to derive or determine the first measured parameter of the lead to be recorded.

At 2210, the medical device position, first electric field, and/or second electric field is varied. In one example, when the lead is in a validation system as described in FIGS. 2-15, in one example, at least one portion of the lead is moved from one opening to a different opening. In examples, the lead is positioned as provided in any one of the positions illustrated in FIGS. 7, 10, and 13. In one example to vary the first electric field and/or second electric field, the frequency of each field is varied.

At 2212, a second measured parameter value of the medical device in the first electric field and second electric field is recorded after varying the medical device position, first electric field, and/or second electric field. In one example, the second measured parameter value is the temperature of the lead that is measured at predetermined positions along the lead within each electric field. In another example the second measured parameter value is the voltage of the lead that again is measured at predetermined positions along the lead within each electric field. In one example the second measured parameter value is measured directly with a sensor such as a temperature sensor or voltage sensor. Alternatively, a measurement of another measured parameter value is detected or measured, and an algorithm is utilized by one or more processors to derive or determine the second measured parameter value of the lead to be recorded.

Thus, provided are validation systems and methods for validating a transfer function of an IMD. By providing validation systems that are able to generate numerous electric fields that may be varied, the amount of readings are increased, increasing testing speeds and efficiencies. Additionally, by providing validation systems that are able to accommodate changes in position of an IMD lead, again, numerous readings and iterations may be achieved with a single validation system and testing session, reducing costs while increasing efficiencies. Additionally, the need for RF coils is eliminated, decreasing cost associated with validation of a transfer function. Therefore, and improved validation system and method are provided.

Closing Statement

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method of validating safety of a medical device in a presence of a magnetic resonance imaging field, the method comprising:
   forming a first electric field with a first electric field generating device;
   forming a second electric field with a second electric field generating device;
   inserting at least a portion of the medical device into the first electric field and into the second electric field at a first position;
   recording a first measured parameter value of the lead in the first electric field and the second electric field in the first position;
   changing at least one of: the medical device position in at least one of the first electric field or the second electric field, the first electric field, or the second electric field; and
   recording a second measured parameter value of the lead in the first electric field and the second electric field after changing the at least one of the medical device position in at least one of the first electric field or the second electric field, the first electric field, or the second electric field;
   validating safety of the medical device based on a comparison related to the first measured parameter value and the second measured parameter value.

2. The method of claim 1, further comprising:
   comparing the recorded first measured parameter value of the medical device to a first predicted parameter value of the lead that is based on a transfer function to determine a first error; and
   comparing the recorded second measured parameter value of the medical device to a second predicted parameter value of the medical device that is based on the transfer function to determine a second error.

3. The method of claim 2, further comprising:
   validating the transfer function based on a model formed utilizing the first error and the second error.

4. The method of claim 2, wherein changing at least one of the medical device position in at least one of the first electric field or the second electric field, the first electric field, or the second electric field includes varying a power source to vary an amplitude, phase, or frequency of the first electric field or second electric field.

5. The method of claim 1, wherein the first electric field generating device is configured to provide the first electric field adjacent an elongated opening in a front panel of the first electric field generating device and the second electric field generating device is configured to provide the second electric field adjacent an elongated opening in a front panel of the second electric field generating device.

6. The method of claim 5, wherein the medical device has at least one lead that includes a first section and a second section, and in the first position the first section of the lead is parallel to the front panel of the first electric field generating device, and in the first position the second section of the lead is parallel to the front panel of the second electric field generating device; and
   wherein in the second position the first section of the lead is angled relative to the front panel of the first electric field generating device, and in the second position the second section of the lead is angled relative to the front panel of the second electric field generating device.

7. The method of claim 1, wherein the first measured parameter value of the medical device is one of medical device temperature, power, e-field, h-field or medical device voltage or current.

8. The method of claim 1, wherein changing the at least one of the medical device position in at least one of the first electric field or the second electric field, the first electric field, or the second electric field includes varying amplitude, or phase, or frequency of the first electric field and/or second electric field.

9. The method of claim 8, wherein the first electric field is configured to change from a first frequency to a second frequency; and wherein the second electric field is configured to change from a first frequency to a second frequency.

10. A method for validating safety of a medical device in a presence of a magnetic resonance imaging (MRI) field, the method comprising:
    forming, with a first electric field generating device, a first electric field;
    forming, with a second electric field generating device, a second electric field in proximity to the first electric field;
    detecting, with sensors, the insertion of at least a portion of the medical device into the first electric field and into the second electric field at a first position;
    calculating predicted parameter values of the medical device based on a transfer function, the transfer function defined to predict a safety characteristic of the medical device when in the presence of an MRI field;
    obtaining measured parameter values from the medical device based on the detecting, the measured parameter values indicative of the safety characteristic of the medical device when exposed to the first and second electric fields; and
    comparing the measured parameter values to the predicted parameter values in connection with validating the transfer function to validate the safety of the medical device.

11. The method of claim 10, further comprising varying, with a power source module of the first electric field generating device, at least one of amplitude, phase, or frequency of the first electric field in response to comparing the measured parameter values to the predicted parameter values in connection with validating the transfer function.

12. The method of claim 10, further comprising determining errors based on comparing the measured parameter values to the predicted parameter values.

13. The method of claim 12, further comprising:
    validating the transfer function based on a model formed utilizing the errors.

14. The method of claim 12, wherein the first electric field generating device is configured to provide the first electric field adjacent an elongated opening in a front panel of the first electric field generating device and the second electric field generating device is configured to provide the second electric field adjacent an elongated opening in a front panel of the second electric field generating device.

15. The method of claim 14, wherein the medical device has at least one lead that includes a first section and a second section, and in the first position the first section of the lead is parallel to the front panel of the first electric field generating device, and in the first position the second section of the lead is parallel to the front panel of the second electric field generating device; and
    wherein in the second position the first section of the lead is angled relative to the front panel of the first electric field generating device, and in the second position the second section of the lead is angled relative to the front panel of the second electric field generating device.

16. The method of claim 10, wherein the first measured parameter value of the medical device is one of medical device temperature, power, e-field, h-field or medical device voltage or current.

17. The method of claim 10, wherein the first electric field is configured to change from a first frequency to a second frequency; and wherein the second electric field is configured to change from a first frequency to a second frequency.

\* \* \* \* \*